United States Patent [19]

Murdock et al.

[11] 4,258,181

[45] Mar. 24, 1981

[54] SUBSTITUTED 9,10-ANTHRACENEBISHYDRAZONES

[75] Inventors: Keith C. Murdock, Pearl River, N.Y.; Frederick E. Durr, Ridgewood, N.J.

[73] Assignee: American Cyanamid Company, Stamford, Conn.

[21] Appl. No.: 36,924

[22] Filed: May 7, 1979

Related U.S. Application Data

[63] Continuation-in-part of Ser. No. 939,591, Sep. 5, 1978, abandoned, which is a continuation-in-part of Ser. No. 855,146, Nov. 28, 1977, abandoned.

[51] Int. Cl.$^3$ ............................................. C07C 109/16
[52] U.S. Cl. .................................. 542/415; 544/152; 544/155; 260/347.2; 544/146; 544/380; 260/347.3; 544/357; 544/88; 260/347.7; 544/96; 544/54; 260/326.55; 544/122; 544/53; 260/326.25; 544/55; 544/294; 260/326.33; 546/187; 546/189; 260/326.83; 546/191; 546/202; 260/326.85; 546/203; 546/283; 260/326.86; 546/284; 546/313; 260/326.9; 546/316; 548/339; 260/333; 548/336; 548/351; 260/239 BC; 549/68; 560/25; 564/18; 564/36; 564/228; 260/455 A; 564/236; 564/251; 564/271; 542/417; 542/418; 544/59; 544/60; 544/79; 544/121; 544/129; 544/130; 544/131; 544/124; 544/139; 544/141
[58] Field of Search ...................... 542/417, 418, 415; 546/187, 189, 191, 202, 203, 283, 284, 313, 316; 260/347.2, 347.3, 347.7, 326.55, 326.25, 326.33, 326.9, 307 F, 333, 306.7 R, 327 R, 239 BC, 566 B, 564 F, 455 A, 552 SC, 554, 556 AR, 329 S, 329 F, 332.2 R, 332.3 R, 332.3 P; 544/79, 58, 59, 129, 60, 121, 130, 155, 131, 124, 139, 152, 141, 146, 380, 357, 88, 96, 54, 122, 53, 55, 294; 548/339, 336, 351; 560/25; 562/28

[56] References Cited

PUBLICATIONS

FINAR Organic Chemistry vol. I; Longmons London, 1963 pp. 162–163.
Thomas et al., J. Med. Chem. 18 (1975), pp. 245–250.

*Primary Examiner*—Arthur P. Demers
*Attorney, Agent, or Firm*—Edward A. Conroy, Jr.

[57] ABSTRACT

This disclosure describes anthracene-9,10-bis-carbonylhydrazones and derivatives thereof useful as antibacterial agents, for inhibiting the growth of transplanted mouse tumors, and for inducing the regression and/or palliation of leukemia and related cancers.

23 Claims, No Drawings

SUBSTITUTED 9,10-ANTHRACENEBISHYDRAZONES

CROSS REFERENCE TO RELATED APPLICATION

This application is a continuation-in-part of our co-pending application Ser. No. 939,591, filed Sept. 5, 1978, now abandoned, which is a continuation-in-part of our abandoned application Ser. No. 855,146, filed Nov. 28, 1977.

BRIEF SUMMARY OF THE INVENTION

This invention relates to new organic compounds and, more particularly, is concerned with novel anthracene-9,10-bis-carbonyl-hydrazones which may be represented by the following general formula:

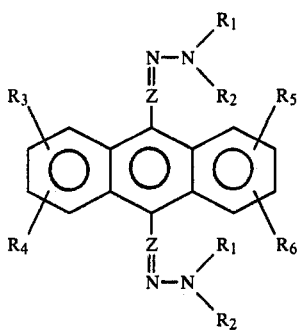
(I)

wherein Z is a moiety of the formulae:

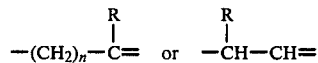

wherein n is 0, 1, 2 or 3 and R is hydrogen, alkyl having up to 4 carbon atoms, cycloalkyl having from 3 to 6 carbon atoms, phenyl or benzyl; $R_1$ is hydrogen or alkyl having up to 4 carbon atoms; $R_2$ is hydrogen, alkyl having up to 4 carbon atoms, phenyl or a moiety of the formulae:

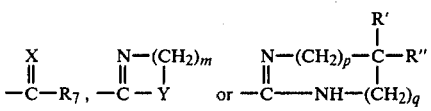

wherein m is 2, 3, 4 or 5, p is 1, 2 or 3, q is 0, 1 or 2, R' is hydrogen or alkyl having up to 4 carbon atoms, R" is hydrogen or alkyl having up to 4 carbon atoms, $R_7$ is alkyl having up to 4 carbon atoms, amino, anilino, hydrazino, monohydroxyalkylamino having from 2 to 4 carbon atoms and wherein the carbon atom alpha to the nitrogen atom may not bear an hydroxy group, alkylamino having up to 4 carbon atoms, dialkylamino wherein each alkyl group has up to 4 carbon atoms, cycloalkylamino having from 3 to 6 carbon atoms, benzylamino, α-phenethylamino, β-phenethylamino, 2-furfurylamino, 3-furfurylamino, α-thenylamino, β-thenylamino, α-pyridylmethylamino, β-pyridylmethylamino, γ-pyridylmethylamino, indanylamino, pyrrolidino, piperidino, morpholino, thiomorpholino, N-methylpiperazino, alkoxy having up to 4 carbon atoms, alkylthio having up to 4 carbon atoms or a moiety of the formula:

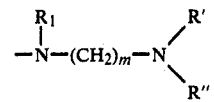

wherein m, $R_1$, R' and R" are as hereinbefore defined and the moiety —NR'R" may be pyrrolidino, piperidino, morpholino or N-methylpiperazino, X is oxo (O=), thioxo (S=) or imino (R'—N= wherein R' is as hereinbefore defined) and Y is oxy (—O—), thio (—S—), methylene (—CH₂—) or a divalent group of the formula:

wherein $R_8$ is alkyl having up to 4 carbon atoms or monohydroxyalkyl having from 2 to 4 carbon atoms and wherein the carbon atom alpha to the nitrogen atom may not bear an hydroxy group; and $R_3$, $R_4$, $R_5$ and $R_6$ are each individually selected from the group consisting of hydrogen, halogen (F, Cl, Br, I), hydroxy, nitro, amino, sulfonamido, alkyl having up to 3 carbon atoms and alkoxy having up to 3 carbon atoms.

The hydrazono substituents pendant from the anthracene-9,10-bis-carbonyl nuclei may be the same or different and may be in the syn or anti forms. Additionally, where the hydrogen atoms or other substituents at positions 1, 4, 5 and 8 of the anthracene nucleus cause restricted rotation of the bonds extending from $C_9$ and $C_{10}$ of the anthracene nucleus, then the entire units

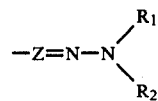

at the $C_9$ and $C_{10}$ positions may be either cis (both extending out from the same face of the anthracene nucleus) or trans (extending out from the opposite faces of the anthracene nucleus). Nuclear magnetic resonance data for the hydrochloride product of Example 3 gives strong evidence for a mixture of rotational isomers at 29° (shows four peaks for —N(CH₃)₂: δ 3.02, 3.05, 3.18 and 3.20) but at 85° C. the four had coalesced to a sharp singlet at 3.20 (in D₂O). The quadruplet reappears on cooling. Thin layer chromatography at 24° C. shows two spots, as also do the products of Examples 7, 8 and 14. Ultra violet absorption data were obtained on the products of Examples 3 and 4 which indicate that the double bonds proximate to the anthracene ring system have been forced out of the plane of that system.

A preferred embodiment of the present invention consists of compounds which may be represented by the following structural formula:

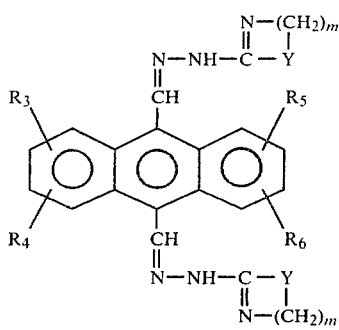

DETAILED DESCRIPTION OF THE INVENTION

The novel compounds of the present invention are obtainable as yellow crystalline materials having characteristic melting points and absorption spectra and which may be purified by recrystallization from common organic solvents such as lower alkanols, dimethylformamide, tetrahydrofuran, methyl isobutyl ketone, and the like.

The organic bases of this invention form non-toxic acid-addition and quaternary ammonium salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. Quaternary ammonium salts may be formed by reaction of the free bases with one or more equivalents of a variety of organic esters of sulfuric, hydrohalic and aromatic sulfonic acids. The organic reagents employed for quaternary ammonium salt formation are preferably lower alkyl halides. However, other organic reagents are suitable for quaternary ammonium salt formation, and may be selected from among a diverse class of compounds including benzyl chloride, phenethyl chloride, naphthylmethyl chloride, dimethyl sulfate, methyl benzenesulfonate ethyl toluenesulfonate, allyl chloride, methallyl bromide and crotyl bromide. For purposes of this invention the free bases are equivalent to their non-toxic acid-addition and quaternary ammonium salts. The acid-addition and quaternary ammonium salts of the organic bases of the present invention are, in general, crystalline solids, relatively soluble in water, methanol and ethanol but relatively insoluble in non-polar organic solvents such as diethyl ether, benzene, toluene, and the like.

The novel compounds of the present invention are useful as antimicrobial agents and possess broad-spectrum antibacterial activity in vitro against a variety of standard laboratory microorganisms as determined by the standard agar well diffusion assay. In this assay, the minimal inhibitory concentration (MIC) was determined by using twofold dilutions of the compound in nutrient agar. One ml. of each dilution was placed in a sterile Petri dish; 9 ml. of nutrient agar was added to each dish. Five-hour cultures of the indicated organism in Trypticase Soy Broth were diluted $10^{-2}$ in nutrient broth. This dilution of each culture was transferred to the surface of the plates by using a Steers replicating device. After incubation at 37° C. for 24 hours, the MIC was recorded as the lowest concentration of the compound which completely inhibits the macroscopic growth of each organism. The MIC of typical compounds of the present invention against the indicated organisms are set forth in Tables I and II below.

TABLE I

| Organism | Minimal Inhibitory Conc. (mcg./ml.) | | | | | |
|---|---|---|---|---|---|---|
| | (1) | (2) | (3) | (4) | (5) | (6) |
| Mycobacterium smegmatis ATCC 607 | 1 | 1 | 50 | 50 | 10 | 2.5 |
| Staphylococcus aureus Rose ATCC 14154 | 25 | 25 | | 25 | 25 | 10 |
| Streptococcus pyogenes C203 | 0.5 | 1 | 25 | 1 | 5 | 2.5 |
| Enterobacter aerogenes 75 | — | — | — | — | — | — |
| Escherichia coli 311 | 25 | 25 | — | — | — | 50 |
| Klebsiella pneumoniae AD | 100 | — | — | — | — | — |
| Proteus vulgaris ATCC 9484 | — | — | — | — | — | — |
| Pseudomonas aeruginosa ATCC 10145 | 50 | — | — | — | — | — |
| Salmonella enteritidis K-12 | 10 | 25 | — | — | — | |

(1) 1,1'-[9,10-Anthrylenebis(methylidynenitrilo)]diguanidine Dihydrochloride
(2) Bis(1,4,5,6-Tetrahydro-2-pyrimidinylhydrazone) of 9,10-anthracenedicarboxaldehyde
(3) 9,10-Anthracenedicarboxaldehyde disemicarbazone
(4) 9,10-Anthracenedicarboxaldehyde bis(thiosemicarbazide)
(5) 1,1'[9,10-Anthrylenebis(methylidynenitrilo)] bis-(3-benzylguanidine)Dihydroiodide
(6) Bis(2-Imidazolin-2-ylmethylhydrazone) of 9,10-Anthracenedicarboxaldehyde Dihydroiodide

TABLE II

| Organism | Minimal Inhibitory Conc. (mcg./ml.) | | | | | |
|---|---|---|---|---|---|---|
| | (1) | (2) | (3) | (4) | (5) | (6) |
| Mycobacterium smegmatis ATCC 607 | 10 | 100 | 2.5 | 10 | 5 | 0.1 |
| Staphyloccoccus aureus Rose ATCC 14154 | — | — | 25 | — | — | 2.5 |
| Streptococcus pyogenes C203 | 25 | — | 0.5 | 10 | — | 0.1 |
| Enterobacter aerogenes 75 | — | — | — | — | — | 25 |
| Escherichia coli 311 | — | — | — | — | — | 25 |
| Klebsiella pneumoniae AD | — | — | — | — | — | 25 |
| Proteus vulgaris ATCC 9484 | — | — | — | — | — | 10 |
| Pseudomonas aeruginosa ATCC 10145 | — | — | — | — | — | — |
| Salmonella enteritidis K-12 | — | — | 25 | — | — | 2.5 |

(1) 9,10-Anthracenedicarboxaldehydediazine with 1,3-dimethyl-2-imidazolidinone Dihydroiodide
(2) 3,3'-[9,10-Anthrylinebis(methylidynenitrilo)] bis-thiocarbazimidic acid Dimethyl Ester Dihydroiodide
(3) 1,1'-[9,10-Anthrylinebis(methylidynenitrilo)] bis-3-methylguanidine Dihydroiodide
(4) N,N-Dimethylglycine(9,10-anthrylinedimethylidyne) dihydrazide Dihydrochloride
(5) Bis(methylhydrazone) of 9,10-Anthracenedicarboxaldehyde Dihydrochloride
(6) Bis(2-Imidazolin-2-ylhydrazone) of 9,10-Anthracenedicarboxaldehyde Dihydrochloride The novel compounds of the present invention also possess the property of inhibiting the growth of transplanted mouse tumors as established by the following tests.

Lymphocytic leukemia P388 test

The animals used are mice all of one sex, weighing a minimum of 17 g. and all within a 3 gram weight range. There are 5 or 6 animals per test group. The tumor transplant is by intraperitoneal injection of 0.1 ml. or 0.5 ml. of dilute ascitic fluid containing $10^6$ cells of lymphocytic leukemia p388. The test compounds are administered intraperitoneally on days one, 5 and 9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil given as a 60 mg./kg. injection. The results of this test with representative compounds of the present invention appear in Table III below. The criterion for efficacy is T/C×100≧125%.

TABLE III
Lymphocytic Leukemia P388 Test

| Compound | Dose (mg./kg.) | Median Survival (Days) | T/C × 100 (Percent) |
|---|---|---|---|
| Bis(2-imidazolin-2-ylhydrazone) of 9,10-anthracenedicarboxaldehyde dihydrochloride | 6 | 23.5 | 214 |
| | 3 | 17.0 | 155 |
| | 1.5 | 20.0 | 182 |
| | 0.75 | 19.0 | 173 |
| | 0.37 | 17.5 | 159 |
| Control | 0 | 11.0 | — |
| 5-Fluorouracil | 60 | | 146–236 |
| 1,1'-[9,10-Anthrylenebis(methylidynenitrilo)]-diguanidine dihydrochloride | 25 | 25.5 | 232 |
| | 12 | 20.0 | 182 |
| | 6 | 18.5 | 168 |
| | 3 | 17.0 | 155 |
| | 1.5 | 16.0 | 145 |
| Control | 0 | 11.0 | — |
| 5-Fluorouracil | 60 | | 146–236 |
| Bis(1,4,5,6-tetrahydro-2-pyrimidinylhydrazone) of 9,10-anthracenedicarboxaldehyde dihydrochloride | 12.5 | 20.0 | 182 |
| | 6.25 | 17.5 | 159 |
| | 3.12 | 18.0 | 164 |
| | 1.56 | 16.5 | 150 |
| | 0.78 | 16.0 | 145 |
| Control | 0 | 11.0 | — |
| 5-Fluorouracil | 60 | | 146–236 |
| 1,1'-[9,10-Anthrylenebis(methylidynenitrilo)]bis(3-benzylguanidine) Dihydroiodide | 25 | 18.5 | 168 |
| | 12.5 | 17.0 | 155 |
| | 3.12 | 16.0 | 145 |
| | 1.56 | 14.5 | 132 |
| | 0.78 | 14.0 | 125 |
| Control | 0 | 11.0 | — |
| 5-Fluorouracil | 60 | | 146–236 |
| 9,10-Anthracenedicarboxaldehyde bis(2-imidazoline-2-ylmethylhydrazone) Dihydroiodide | 5.26 | 23.5 | 214 |
| | 3.12 | 20.0 | 182 |
| | 1.56 | 17.5 | 159 |
| | 0.78 | 16.0 | 145 |
| Control | 0 | 11.0 | — |
| 5-Fluorouracil | 60 | | 146–236 |
| 1,1'-[9,10-Anthrylenebis(methylidynenitrilo)]bis(3-methylguanidine) Dihydroiodide | 25 | 29 | 264 |
| | 12.5 | 25 | 227 |
| | 6.25 | 22 | 200 |
| | 3.12 | 17 | 155 |
| | 1.56 | 19 | 173 |
| | 0.78 | 15.5 | 141 |
| Control | 0 | 11 | |
| 5-Fluorouracil | 60 | | 146–236 |
| Bis(4,5,6,7-tetrahydro-1H-1,3-diazepin-2-ylhydrazone) of 9,10-anthracenedicarboxaldehyde Dihydroiodide | 12.5 | 19.0 | 190 |
| | 6.25 | 18.0 | 180 |
| | 3.12 | 17.0 | 170 |
| | 1.56 | 16.5 | 165 |
| | 0.78 | 16.0 | 160 |
| Control | 0 | 10 | |
| 5-Fluorouracil | 40 | 20 | 200 |
| 1,1'-(9,10-Anthrylenebis)methylidynenitrilo)]-bis(1-methylguanidine)Dihydrobromide | 12.5 | 21.0 | 191 |
| | 6.25 | 17.5 | 159 |
| | 3.12 | 15.0 | 136 |
| Control | 0 | 11 | |
| 5-Fluorouracil | 40 | 17.5 | 159 |
| 1,1'-[9,10-Anthrylenebis(methylidynenitrilo)]-bis[3,3-dimethylguanidine]Dihydrochloride | 6.25 | 22.5 | 205 |
| | 3.12 | 21.5 | 195 |
| | 1.56 | 18.0 | 164 |
| | 0.78 | 19.0 | 173 |
| Control | 0 | 11 | |
| 5-Fluorouracil | 40 | 19 | 165 |
| 1,1'-[9,10-Anthrylenebis(methylidynenitrilo)]-bis[1,3-dimethylguanidine]Dihydroiodide | 6.25 | 24.0 | 218 |
| | 3.12 | 19.0 | 173 |
| | 1.56 | 19.0 | 173 |
| | 0.78 | 17.5 | 159 |
| Control | 0 | 11 | |
| 5-Fluorouracil | 40 | 19 | 165 |
| 1,1'-[9,10-Anthrylenebis(methylidynenitrilo)]-bis[3-(2-hydroxyethyl)guanidine]Dihydroiodide | 25 | 19.0 | 190 |
| | 12.5 | 19.0 | 190 |
| | 6.25 | 16.0 | 160 |
| | 3.12 | 15.0 | 150 |
| Control | 0 | 10 | |
| 5-Fluorouracil | 40 | 16.5 | 165 |

TABLE III-continued

Lymphocytic Leukemia P388 Test

| Compound | Dose (mg./kg.) | Median Survival (Days) | T/C × 100 (Percent) |
|---|---|---|---|
| Bis(2-imidazolin-2-ylhydrazone) of 2-Chloro-9,10-anthracenedicarboxaldehyde Dihydrochloride | 12.5 | 21.0 | 200 |
| | 6.25 | 20.0 | 190 |
| | 3.12 | 20.5 | 195 |
| | 1.56 | 19.0 | 181 |
| | 0.78 | 18.5 | 176 |
| Control | 0 | | |
| 5-Fluorouracil | 40 | | 181 |
| Bis(2-imidazolin-2-ylhydrazone) of 2-methyl-9,10-anthracenedicarboxaldehyde Dihydrochloride | 12.5 | 22.0 | 210 |
| | 6.25 | 20.0 | 190 |
| | 3.12 | 21.0 | 200 |
| | 1.56 | 18.0 | 171 |
| Control | 0 | 10.5 | |
| 5-Fluorouracil | 40 | 19.0 | 181 |
| 4-Morpholinecarboximidic acid, 2,2'(9,10-Anthrylenedimethylidyne)hydrazide Dihydroiodide | 50 | 18.0 | 157 |
| | 25 | 16.0 | 139 |
| | 12.5 | 15.5 | 135 |
| Control | 0 | 11.5 | |
| 5-Fluorouracil | 40 | 19.0 | 165 |
| Bis[1-(2-hydroxypropyl)-2-imidazolin-2-ylhydrazone] of 9,10-anthracenedicarboxaldehyde Dihydroiodide | 25 | 13.5 | 135 |
| | 12.5 | 13.0 | 130 |
| Control | 0 | 10 | |
| 5-Fluorouracil | 40 | 18 | 180 |
| Bis(2-imidazolin-2-ylhydrazone) of 1,4-dimethoxy-9,10-anthracenedicarboxaldehyde Dihydrochloride | 50 | 17.5 | 159 |
| Control | 0 | 11 | |
| 5-Fluorouracil | 40 | 17.5 | 159 |
| 1,1'-[9,10-Anthrylenebis(methylidyne)]-bis[3-furfurylguanidine]Dihydrochloride | 25 | 17.5 | 159 |
| | 12.5 | 17.5 | 159 |
| | 6.25 | 17.5 | 159 |
| | 3.12 | 16.0 | 145 |
| Control | 0 | 11 | |
| 5-Fluorouracil | 40 | 17.5 | 159 |
| 1,1'-[9,10-Anthrylenebis(methylidynetrilo)]bis[2,3-diisopropylguanidine] Dihydroiodide | 50 | 16.0 | 152 |
| | 25 | 13.5 | 129 |
| Control | 0 | 10.5 | |
| 5-Fluorouracil | 60 | 14.5 | 138 |
| 1,1'-[9,10-Anthrylenebis(methylidynenitrilo)]bis[3-(2-thenyl)guanidine Dihydrochloride | 25 | 19.0 | 190 |
| | 12.5 | 18.0 | 180 |
| | 6.25 | 18.0 | 180 |
| | 3.12 | 16.5 | 165 |
| | 1.56 | 16.0 | 160 |
| Control | 0 | 10 | |
| 5-Fluorouracil | 60 | 20.5 | 205 |
| 1,1'[9,10-Anthrylenebis(methylidynenitrilo)]bis[3-(1-indanyl)guanidine] Dihydroiodide | 200 | 18.0 | 180 |
| | 100 | 16.5 | 165 |
| | 50 | 14.0 | 140 |
| | 25 | 14.0 | 140 |
| Control | 0 | 10 | |
| 5-Fluorouracil | 60 | 20 | 200 |
| 1,1'-[9,10-Anthrylenebis(methylidynenitrilo)]bis[3-(4-pyridylmethyl)guanidine]tetrahydroiodide | 25 | 18.5 | 185 |
| | 12.5 | 19.0 | 190 |
| | 6.25 | 18.0 | 180 |
| | 3.12 | 16.0 | 160 |
| Control | 0 | 10 | |
| 5-Fluorouracil | 60 | 20 | 200 |
| 9,10-Anthracenedicarboxaldehyde bis(thiosemicarbazone) | 100 | 16.0 | 145 |
| | 50 | 15 | 136 |
| Control | 0 | 11 | |
| 5-Fluorouracil | 60 | 15 | 136 |
| 1,1'-[9,10-Anthrylenebis(methylidynenitrilo)]bis(3-cyclohexylguanidine)Dihydroiodide | 50 | 19 | 173 |
| | 25 | 18 | 164 |
| | 12.5 | 18 | 164 |
| | 6.25 | 15.5 | 141 |
| | 3.12 | 15 | 136 |
| Control | 0 | 11 | |
| 5-Fluorouracil | 60 | | 146–236 |
| Bis(2-imidazolin-2-ylhydrazone) of 2,6-difluoro-9,10-anthracenedicarboxaldehyde dihydrochloride | 12.5 | 20.0 | 182 |
| | 6.25 | 19.0 | 173 |
| | 3.12 | 19.5 | 177 |
| | 1.56 | 18.5 | 168 |
| | 0.78 | 17.5 | 159 |
| Control | 0 | 11.0 | |
| 5-Fluorouracil | 60 | 16.0 | 145 |
| Bis(2-imidazolin-2-ylhydrazone) of 2,3-dimethyl-9,10-anthracenedicarboxaldehyde dihydrochloride | 100 | 18.0 | 164 |
| | 50 | 18.0 | 164 |

TABLE III-continued

| Lymphocytic Leukemia P388 Test | | | |
|---|---|---|---|
| Compound | Dose (mg./kg.) | Median Survival (Days) | T/C × 100 (Percent) |
| | 25 | 18.0 | 164 |
| | 12.5 | 15.0 | 136 |
| | 6.25 | 14.5 | 132 |
| Control | 0 | 11.0 | |
| 5-Fluorouracil | 60 | 15.5 | 141 |
| Bis(2-imidazolin-2-ylhydrazone) of 1,4-dimethyl-9,10-anthracenedicarboxaldehyde dihydrochloride | 18.8 | 16.5 | 157 |
| | 9.4 | 15.0 | 143 |
| | 4.7 | 14.0 | 133 |
| Control | 0 | 10.5 | |
| 5-Fluorouracil | 60 | 19.5 | 186 |
| Bis(2-imidazolin-2-ylhydrazone) of 1,5-difluoro-9,10-anthracenedicarboxaldehyde, dihydrochloride | 100 | 24.0 | 240 |
| | 50 | 21.0 | 210 |
| | 25 | 20.5 | 205 |
| | 12.5 | 21.5 | 215 |
| | 6.25 | 19.0 | 190 |
| Control | 0 | 10.0 | |
| 5-Fluorouracil | 60 | 18.0 | 180 |
| Bis(2-imidazolin-2-ylhydrazone) of 2-fluoro-9,10-anthracenedicarboxaldehyde, dihydrochloride | 6.25 | 24.5 | 223 |
| | 3.12 | 24.5 | 223 |
| | 1.56 | 21.0 | 191 |
| | 0.78 | 21.0 | 191 |
| Control | 0 | 11.0 | |
| 5-Fluorouracil | 60 | 18.0 | 164 |
| Bis(2-imidazolin-2-ylhydrazone) of 1-fluoro-9,10-anthracenedicarboxaldehyde, dihydrochloride | 6.25 | 18.0 | 180 |
| | 3.12 | 19.5 | 195 |
| | 1.56 | 21.5 | 215 |
| | 0.78 | 17.5 | 175 |
| Control | 0 | 10.0 | |
| 5-Fluorouracil | 60 | 19.0 | 190 |
| Bis(2-imidazolin-2-ylhydrazone) of 1-chloro-9,10-anthracenedicarboxaldehyde, dihydrochloride | 12.5 | 27.5 | 250 |
| | 6.25 | 31.5 | 286 |
| | 3.12 | 26.5 | 241 |
| | 1.56 | 23.5 | 214 |
| | 0.78 | 19.0 | 173 |
| Control | 0 | 11.0 | |
| 5-Fluorouracil | 60 | 18.0 | 164 |
| Bis(2-imidazolin-2-ylhydrazone) of 1-chloro-2-methyl-9,10-anthracenedicarboxaldehyde, dihydrochloride | 12.5 | 23.0 | 230 |
| | 6.25 | 20.0 | 200 |
| | 3.12 | 18.0 | 180 |
| | 1.56 | 18.0 | 180 |
| Control | 0 | 10.0 | |
| 5-Fluorouracil | 60 | 12.0 | 120 |
| 1,1'-[2-Chloro-9,10-anthrylenebis(methylidyne-nitrilo)]bis[3,3-dimethylguanidine] dihydroiodide | 12.5 | 20.0 | 182 |
| | 6.25 | 18.0 | 164 |
| | 3.12 | 17.5 | 159 |
| | 1.56 | 15.5 | 141 |
| Control | 0 | 11.0 | |
| 5-Fluorouracil | 60 | 18.0 | 164 |
| Bis(1,4,5,6-tetrahydro-2-pyrimidinylhydrazone) of 2-chloro-9,10-anthracenedicarboxaldehyde, dihydrochloride | 6.25 | 18.5 | 185 |
| | 3.12 | 22.5 | 225 |
| | 1.56 | 18.0 | 180 |
| | 0.78 | 18.0 | 180 |
| Control | 0 | 10.0 | |
| 5-Fluorouracil | 60 | 22.0 | 220 |
| 1,1'-[9,10-Anthrylenebis(methylidynenitrilo)]bis-[3-(4-pyridylmethyl)guanidine] tetrahydrochloride | 25 | 18.5 | 185 |
| | 12.5 | 17.5 | 175 |
| | 6.25 | 18.0 | 180 |
| | 3.12 | 17.0 | 170 |
| Control | 0 | 10.0 | |
| 5-Fluorouracil | 60 | 19.0 | 190 |
| 1,1'-[9,10-Anthrylenebis(methylidynenitrilo)]bis-[3-(3-pyridylmethyl)guanidine] tetrahydrochloride | 25 | 23.5 | 214 |
| | 12.5 | 22.0 | 200 |
| | 6.25 | 18.5 | 168 |
| | 3.12 | 18.0 | 164 |
| Control | 0 | 11.0 | |
| 5-Fluorouracil | 60 | 18.0 | 164 |
| 1,1'-[9,10-Anthrylenebis(methylidynenitrilo)]bis-[3-(2-pyridylmethyl)guanidine] tetrahydrochloride | 50 | 19.5 | 195 |
| | 25 | 19.0 | 190 |
| | 12.5 | 19.0 | 190 |
| | 6.25 | 19.5 | 195 |
| | 3.12 | 16.0 | 160 |
| Control | 0 | 10.0 | |
| 5-Fluorouracil | 60 | 18.0 | 180 |
| Bis(2-imidazolin-2-ylhydrazone) of 2-ethyl-9,10-anthracenedicarboxaldehyde, dihydrochloride | 12.5 | 17.0 | 155 |
| | 6.25 | 18.0 | 164 |
| | 3.12 | 18.0 | 164 |
| | 1.56 | 17.0 | 155 |
| | 0.78 | 16.5 | 150 |

TABLE III-continued

Lymphocytic Leukemia P388 Test

| Compound | Dose (mg./kg.) | Median Survival (Days) | T/C × 100 (Percent) |
|---|---|---|---|
| Control | 0 | 11.0 | |
| 5-Fluorouracil | 60 | 16.0 | 145 |
| 9,10-Anthracenedicarboxaldehyde, bis(4,5,6,7-tetrahydro-3H-azepin-2-ylhydrazone, dihydrochloride | 25 | 21.5 | 195 |
| | 12.5 | 16.0 | 145 |
| Control | 0 | 11.0 | |
| 5-Fluorouracil | 60 | 20.5 | 186 |
| 1,1'-[9,10-Anthrylenebis(methylidynenitrilo]bis[3-(2-dimethylaminoethyl)guanidine] tetrahydrochloride | 3.12 | 13.0 | 130 |
| Control | 0 | 10.0 | |
| 5-Fluorouracil | 60 | >19 | >190 |
| 9,10-Anthracenedicarboxaldehyde, bis[4-(3-dimethylaminopropyl)-3-thiosemicarbazone] dihydrochloride | 6.25 | 17.0 | 170 |
| | 3.12 | 16.5 | 165 |
| | 1.56 | 17.5 | 175 |
| | 0.78 | 16.0 | 160 |
| Control | 0 | 10.0 | |
| 5-Fluorouracil | 60 | 21.0 | 210 |
| 9,10-Anthracenedicarboxaldehyde, bis(4,4-dimethyl-2-imidazolin-2-ylhydrazone) dihydrochloride | 12.5 | 22.0 | 220 |
| | 6.25 | 21.0 | 210 |
| | 3.12 | 20.0 | 200 |
| | 1.56 | 19.0 | 190 |
| | 0.78 | 17.5 | 175 |
| Control | 0 | 10.0 | |
| 5-Fluorouracil | 60 | 21.0 | 210 |
| 9,10-Anthracenedicarboxaldehyde, bis[(1,4,5,6-tetrahydro-5,5-dimethyl-2-pyrimidinyl)hydrazone] dihydrochloride | 200 | 28.0 | 255 |
| | 100 | 33.5 | 305 |
| | 50 | 31.0 | 282 |
| | 25 | 23.5 | 214 |
| | 12.5 | 22.0 | 200 |
| Control | 0 | 11.0 | |
| 5-Fluorouracil | 60 | 18.0 | 164 |

Lymphocytic leukemia L1210 test

The procedure is the same as for the Lymphocytic leukemia P388 test except that the tumor transplant consists of lymphocytic leukemia L1210 inoculated at a concentration of $10^5$ cells/mouse with a mean survival time being calculated, and the test compound is administered only on day one. The results of this test with a representative compound of this invention appear in Table IV below. The criterion for efficacy is T/C×100≧125%.

TABLE IV

Lymphocytic Leukemia L1210 Test

| Compound | Dose (mg./kg.) | Median Survival (Days) | T/C × 100 (Percent) |
|---|---|---|---|
| Bis(2-imidazolin-2-ylhydrazone) of 9,10-anthracenedicarboxaldehyde dihydrochloride | 100 | 10.2 | 134 |
| | 50 | 11.6 | 153 |
| | 25 | 10.4 | 137 |
| | 12 | 10.4 | 137 |
| | 6 | 10.8 | 142 |
| Control | 0 | 7.6 | — |
| 5-Fluorouracil | 200 | 14.4 | 189 |

Melanotic Melanoma B16

The animals used are C57BC/6 mice, all of the same sex, weighing a minimum of 17 g. and all within a 3 g. weight range. There are normally 10 animals per test group. A one-gram portion of malanotic melanoma B16 tumor is homogenized in 10 ml. of cold balanced salt solution and a 0.5 ml. aliquot of the homogenate is implanted intraperitoneally into each of the test mice. The test compounds are administered intraperitoneally on days one through 9 (relative to tumor inoculation) at various doses. The animals are weighed and survivors are recorded on a regular basis for 60 days. The median survival time and the ratio of survival time for treated (T)/control (C) animals are calculated. The positive control compound is 5-fluorouracil given as a 20 mg./kg. injection. The results of this test with representative compounds of the present invention appear in Table V below. The criterion for efficacy is T/C×100≧125%.

TABLE V

Melanotic Melanoma B16

| Compound | Dose (mg./kg.) | Median Survival (Days) | T/C × 100 (Percent) |
|---|---|---|---|
| Bis(2-imidazolin-2-ylhydrazone) of 9,10-anthracenedicarboxaldehyde dihydrochloride | 3.1 | 35.5 | 222 |
| | 1.5 | 31.0 | 194 |
| | 0.78 | 26.5 | 166 |
| | 0.3 | 23.5 | 147 |
| Control | 0 | 16.0 | — |
| 5-Fluorouracil | 20 | 26.0 | 163 |
| 1,1'-[9,10-Anthrylenebis(methylidynenitrilo)]- | 12.5 | 21.0 | 135 |

TABLE V-continued

Melanotic Melanoma B16

| Compound | Dose (mg./kg.) | Median Survival (Days) | T/C × 100 (Percent) |
|---|---|---|---|
| diguanidine dihydrochloride | 1.5 | 21.0 | 131 |
| Control | 0 | 16.0 | — |
| 5-Fluorouracil | 20 | 27.5 | 172 |
| Bis(1,4,5,6-tetrahydro-2-pyrimidinylhydrazone) of 9,10-anthracenedicarboxaldehyde dihydrochloride | 6.2 | 31.0 | 148 |
| | 3.1 | 32.0 | 152 |
| | 1.5 | 33.5 | 160 |
| Control | 0 | 21.0 | — |
| 5-Fluorouracil | 50 | 29.5 | 140 |
| Bis(2-imidazolin-2-ylmethylhydrazone) of 9,10-Anthracenedicarboxaldehyde Dihydroiodide | 3 | 37.5 | 221 |
| | 1.5 | 36.0 | 212 |
| | 0.7 | 32.5 | 191 |
| Control | 0 | 17.0 | |
| 5-Fluorouracil | 20 | 28 | 165 |
| 1,1'[9,10-Anthrylenebis(methylidynenitrilo)]bis[3-(2-hydroxyethyl)guanidine Dihydroiodide | 12 | 30.0 | 172 |
| | 6 | 29.5 | 170 |
| | 3 | 25.5 | 147 |
| | 1.5 | 22.0 | 126 |
| Control | 0 | 17.4 | |
| 5-Fluorouracil | 20 | 28.0 | 161 |
| Bis(2-imidazolin-2-ylhydrazone) of 2-methyl-9,10-anthracenedicarboxaldehyde Dihyrochloride | 62 | 49.0 | 272 |
| | 3.1 | 43.0 | 239 |
| | 1.56 | 44.0 | 244 |
| | 0.5 | 27.0 | 150 |
| Control | 0 | 18.0 | |
| 5-Fluorouracil | 20 | 32.5 | 181 |
| Bis(2-imidazolin-2-ylhydrazone) of 2-chloro-9,10-anthracenedicarboxaldehyde Dihydrochloride | 6.2 | 50.5 | 306 |
| | 3.1 | 45.0 | 273 |
| | 1.56 | 33.0 | 200 |
| | 0.5 | 35.5 | 215 |
| | 0.25 | 28.0 | 170 |
| Control | | 16.5 | |
| 5-Fluorouracil | 20 | 27.5 | 167 |
| 1,1'-[9,10-Anthrylenebis(methylidynenitrilo)]-bis-3-methylguanidine Dihyroiodide | 12.5 | 41.5 | 244 |
| | 6.2 | 32.5 | 191 |
| | 3.1 | 13.0 | 76 |
| | 1.56 | 33.0 | 194 |
| Control | 0 | 17.0 | |
| 5-Fluorouracil | 20 | 27.0 | 159 |
| 1,1'[9,10-Anthrylenebis(methylidynenitrilo)]-bis(1,3-dimethylguanidine) Dihydrochloride | 3.1 | 36.5 | 192 |
| | 1.5 | 40.0 | 211 |
| | 0.5 | 35.0 | 184 |
| | 0.25 | 31.5 | 166 |
| | 0.1 | 29.0 | 153 |
| Control | 0 | 19.0 | |
| 5-Fluorouracil | 20 | 29.0 | 153 |
| 1,1'-[9,10-Anthrylenebis(methylidynenitrilo)]-bis(3,3-dimethylguanidine) Dihydroiodide | 3.1 | 43.5 | 229 |
| | 1.5 | 40.5 | 213 |
| | 0.5 | 35.5 | 187 |
| | 0.25 | 26.0 | 137 |
| Control | 0 | 19.0 | |
| 5-Fluorouracil | 20 | 29.0 | 153 |
| Bis(4,5,6,7-tetrahydro-1H-1,3-diazepin-2-ylhydrazone) of 9,10-anthracenedicarboxaldehyde Dihydroiodide | 12.5 | 45.0 | 273 |
| | 6.2 | 40.5 | 245 |
| | 3.1 | 36.0 | 218 |
| | 1.56 | 30.5 | 185 |
| | 0.5 | 26.0 | 158 |
| Control | 0 | 16.5 | |
| 5-Fluorouracil | 20 | 27.5 | 167 |
| 1,1'-[9,10-Anthrylenebis(methylidyne)]-bis(3-furfurylguanidine) Dihydrochloride | 12.5 | >60 | >267 |
| | 6.2 | 47 | 209 |
| | 3.1 | 42 | 187 |
| | 1.56 | 31 | 138 |
| Control | 0 | 22.5 | |
| 5-Fluorouracil | 20 | 30.0 | 133 |
| 1,1'-[9,10-Anthrylenebis(methylidynenitrilo)]bis-[3-(4-pyridylmethyl)guanidine] tetrahydroiodide | 25 | 36.0 | 211 |
| | 12.5 | 35.5 | 208 |
| | 6.2 | 31.5 | 185 |
| | 3.1 | 30.0 | 176 |
| | 1.56 | 27.5 | 162 |
| Control | 0 | 17.0 | |
| 5-Fluorouracil | 20 | 27.0 | 159 |
| Bis(2-imidazolin-2-ylhydrazone) of 2,6-difluoro-9,10-anthracenedicarboxaldehyde, dihydrochloride | 6 | 38.5 | 167 |
| | 3 | 50.0 | 217 |
| | 1.5 | 41.0 | 178 |
| | 0.5 | 32.0 | 139 |
| Control | 0 | 23.0 | |
| 5-Fluorouracil | 20 | 27.5 | 120 |
| Bis[2-imidazolin-2-ylhydrazone] of 2,3-dimethyl- | 50 | 29.5 | 173 |

TABLE V-continued

Melanotic Melanoma B16

| Compound | Dose (mg./kg.) | Median Survival (Days) | T/C × 100 (Percent) |
|---|---|---|---|
| 9,10-anthracenedicarboxaldehyde, dihydrochloride | 25 | 28.0 | 165 |
| | 12 | 29.5 | 173 |
| | 6 | 30.0 | 176 |
| | 3 | 26.5 | 156 |
| Control | 0 | 17.0 | |
| 5-Fluorouracil | 20 | 27.0 | 159 |
| Bis(1,4,5,6-tetrahydro-2-pyrimidinylhydrazone) of 2-chloro-9,10-anthracenedicarboxaldehyde, dihydrochloride | 6.0 | >49 | >272 |
| | 3.0 | >53 | >294 |
| | 1.5 | 33.0 | 183 |
| | 0.5 | 33.0 | 183 |
| Control | 0 | 18.0 | |
| 5-Fluorouracil | 20 | 26.0 | 144 |
| 1,1'-[2-Chloro-9,10-anthrylenebis(methylidynenitrilo)]diguanidine, dihydrochloride | 25 | 30.5 | 203 |
| | 12 | 30.0 | 200 |
| | 6 | 32.0 | 213 |
| | 3 | 26.5 | 177 |
| | 1.5 | 23.0 | 153 |
| Control | 0 | 15.0 | |
| 5-Fluorouracil | 20 | 24.5 | 163 |

Solutions of the active ingredient as a free base or salt can be prepared in water or in water suitably mixed with, for example, surfactants. The preferred compound, where m is 2 and y is imino in formula (II), is slightly soluble in water. It can, for example, be converted to an acetate having a pH in aqueous solution of about 7.4 which, on analysis, shows about one acetic acid residue per anthracene nucleus. A diacetate may also be produced having a pH in aqueous solution of about 6.2. The diacetate is soluble in water to the extent of about 400 milligrams per milliliter of water. The base or various salts may be made more soluble by the addition of surfactants such as hydroxypropylcellulose to the composition. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical compositions can be in forms suitable for injectable use, which forms include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredient or ingredients in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coattings, antibacterial and antifungal agents, isotonic and absorption delaying agents and the like. The use of such media and agents for pharmaceutical active substances is well known in the art. Except insofar as any conventional media or agent is incompatable with the active ingredient, its use in the present compositions is contemplated. Supplementary active ingredients can also be incorporated into the inventive compositions.

It is especially advantageous to formulate compositions in dosage unit form for ease of administration and uniformity of dosage. Dosage unit form as used in the specification and claims herein refers to physically discrete units suited as unitary dosages for the animal subjects to be treated, each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as disclosed in detail in this specification.

The dosage of the principal active ingredient for the treatment of the indicated conditions depends upon the age, weight and condition of the subject being treated;

the particular condition and its severity; the particular form of the active ingredient and the route of administration. A daily dose of from about one to about 100 mg./kg. of body weight given singly or in divided doses of up to 5 times a day embraces the effective range for the treatment of most conditions for which the novel compounds are effective and substantially non-toxic. For a 75-kg. subject, this translates into between about 75 and about 7500 mg./day. If the dosage is divided, for example, into 3 individual dosages, these will range from about 25 to about 2500 mg. of the active ingredient. The preferred range is from 2 to about 50 mg./kg. of body weight/day with about 2 to about 30 mg./kg./day being more preferred.

The principal active ingredient is compounded for convenient and effective administration in effective amounts with a suitable pharmaceutically-acceptable carrier in dosage unit form as hereinbefore disclosed. A unit dosage form can, for example, contain the principal active ingredient in amounts ranging from about 0.1 to about 400 mg., with from about one to about 30 mg. being preferred. Expressed in proportions, the active ingredient is generally present in from about 0.1 to about 400 mg./ml. of carrier. In the case of compositions containing supplementary active ingredients, the dosages are determined by reference to the usual dose and manner of administration of the said ingredients.

Most of the novel compounds of the present invention may be readily prepared as set forth in the following reaction scheme:

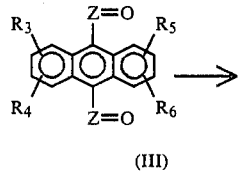

(III)

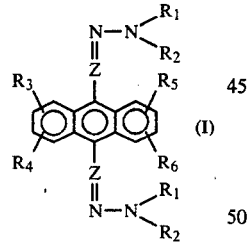

(I)

wherein Z, $R_1$, $R_2$, $R_3$, $R_4$, $R_5$ and $R_6$ are as hereinabove defined. In accordance with the above reaction scheme, an appropriately substituted, 9,10-anthracenedialdehyde or diketone (III) is reacted with a hydrazine derivative of the formula: $H_2H-NR_1R_2$ to provide the 9,10-anthracene-bis-hydrazones (I). The reaction is carried out in a lower alkanol in the presence of an acid such as hydrochloric, hydriodic or acetic (or glacial acetic acid may be used as the sole solvent) usually at the reflux temperature of the reaction mixture.

The starting 9,10-anthracenedialdehydes and ketones may be obtained commercially or prepared in accordance with any one of the reaction schemes denominated (A), (B) and (C) below wherein $R_3$, $R_4$, $R_5$ and $R_6$ are as hereinabove defined.

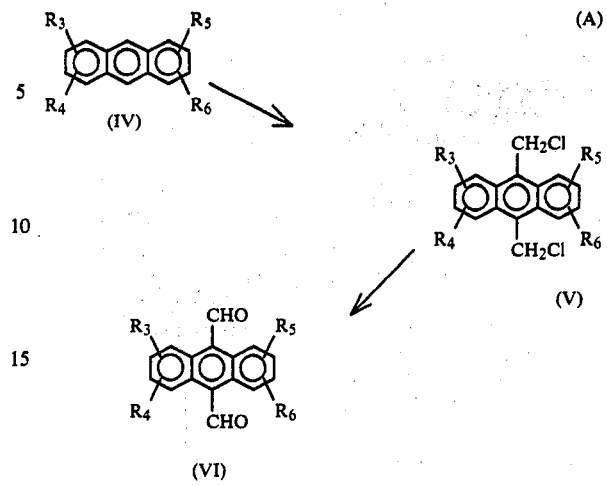

In accordance with the above reaction scheme, the anthracene derivative (IV) suspended in dioxane and concentrated hydrochloric acid and saturated with HCl, is treated with paraformaldehyde at the reflux temperature for 2–6 hours to obtain the 9,10-bis-(chloromethyl)anthracene derivative (V). This 9,10-bis-(chloromethyl)anthracene, suspended in dry dimethyl sulfoxide under nitrogen at room temperature, is treated with sodium in ethanol and worked up as described in the examples to obtain the desired 9,10-anthracene dicarboxaldehyde (VI).

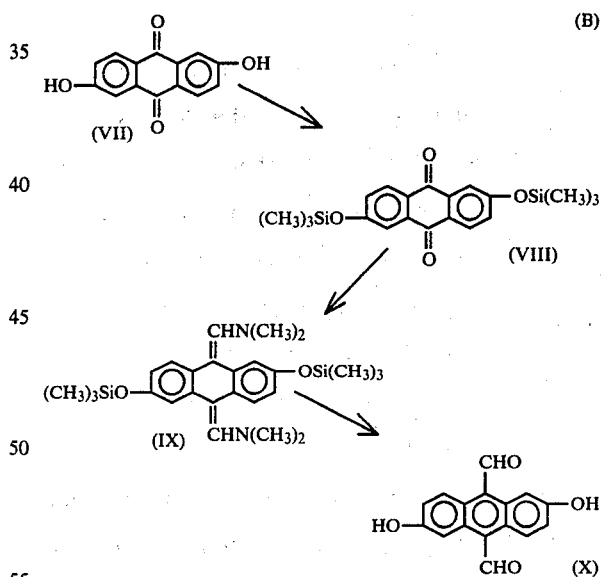

In accordance with the above reaction scheme, the dihydroxyanthraquinone (VII) is treated with trimethylsilyl chloride in dry tetrahydrofuran in the presence of triethylamine to obtain the trimethylsilyloxy derivative (VIII). The latter compound is then dissolved in tetrahydrofuran and treated with an anhydrous diethyl ether-hexane solution of [α-lithio-α-(N,N-dimethylamino)methyl]diphenylphosphine oxide at room temperature to obtain the bis-enamine (IX) which, without isolation, is hydrolyzed by the addition of a 90% formic acid solution to give the hydroxy substituted 9,10-anthracenedicarboxaldehyde (X).

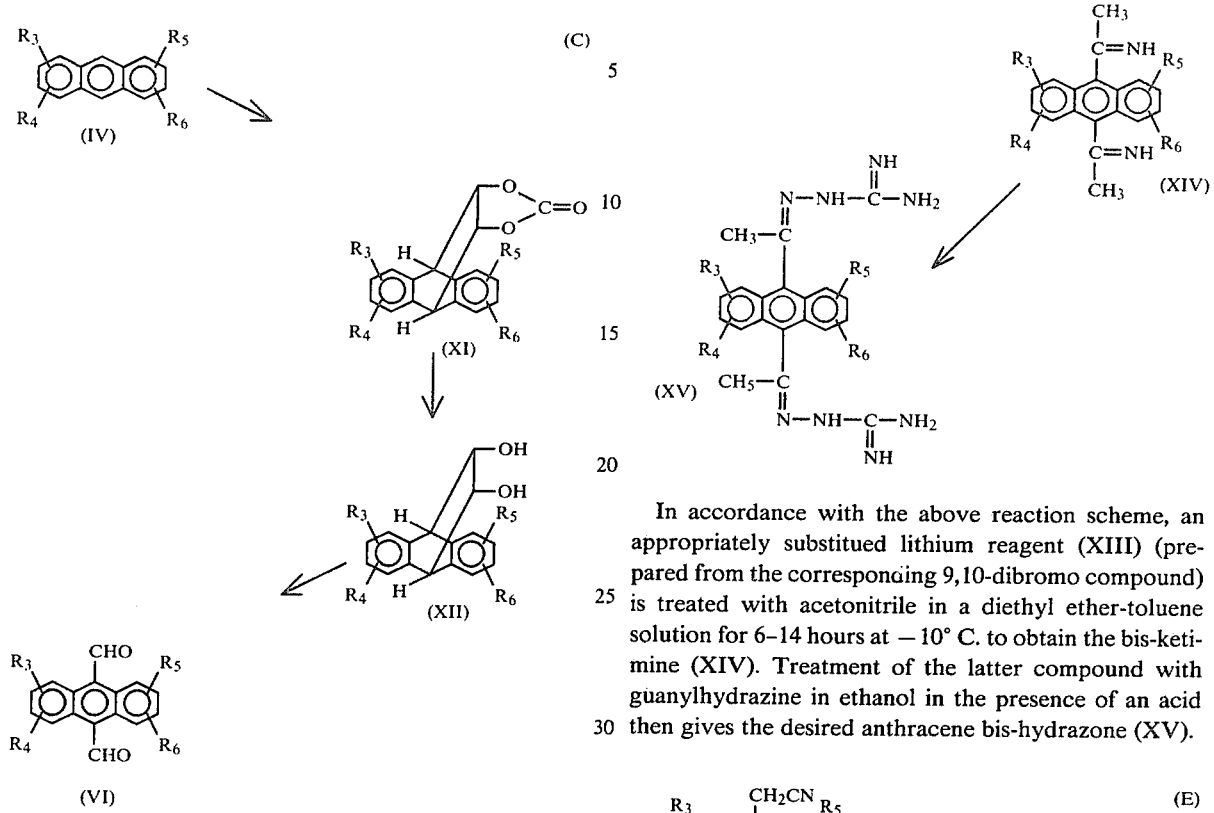

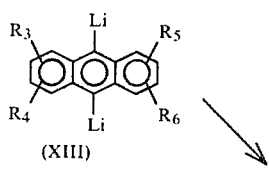

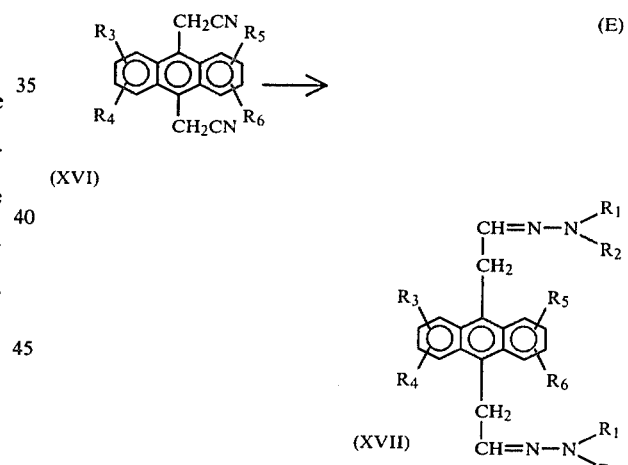

In accordance with the above reaction scheme, the anthracene derivative (IV) is heated with excess vinylene carbonate under reflux for about 20 hours to give the cyclic carbonate (XI). Hydrolysis of the cyclic carbonate (XI) with aqueous-ethanolic potassium hydroxide at 75° C. for about 2 hours produces the diol (XII) which in turn is treated with lead tetraacetate in acetic acid at 35° C. for about 2 hours to give the 9,10-anthracenedicarboxaldehyde (VI).

Certain anthracene bis-hydrazones are more readily prepared by methods other than the general method previously outlined. Two of these are outlined as reaction schemes (D) and (E) below wherein $R_3$, $R_4$, $R_5$ and $R_6$ are as hereinabove defined:

In accordance with the above reaction scheme, an appropriately substitued lithium reagent (XIII) (prepared from the corresponding 9,10-dibromo compound) is treated with acetonitrile in a diethyl ether-toluene solution for 6–14 hours at $-10°$ C. to obtain the bis-ketimine (XIV). Treatment of the latter compound with guanylhydrazine in ethanol in the presence of an acid then gives the desired anthracene bis-hydrazone (XV).

In accordance with the above reaction scheme, a mixture of 9,10-anthracenediacetonitrile derivative (XVI and a substituted hydrazine hydrochloride, sodium acetate and Raney-nickel in ethanol is reduced with hydrogen until 2 molar equivalents of hydrogen have been absorbed to give the desired anthracene bis-hydrazone (XVII). The novel monohydroxyanthracene-9,10-bis-hydrazones and the dihydroxyanthracene-9,10-bis-hydrazones of the present invention may be prepared as set forth in reaction schemes (B) and (C) after having converted the hydroxy groups to trimethylsilyloxy derivatives as in formula (VIII) of reaction scheme (B).

The invention will be described in greater detail in conjunction with the following specific examples.

EXAMPLE 1

Bis(2-imidazolin-2-ylhydrazone) of 9,10-anthracenedicarboxaldehyde dihydrochloride The 2-hydrazino-2-imidazoline monohydrochloride, described in U.S. Pat. No. 3,931,152, is converted to the dihydrochloride by treatment with ethanol and concentrated hydrochloric acid. A suspension of 3.46 g. of the 2-hydrazino-2-imidazoline dihydrochloride and 2.34 g. of 9,10-anthracenedicarboxaldehyde in 100 ml. of ethanol is stirred and heated under reflux for two hours. The mixture is cooled and the solid is collected and washed with ethanol giving the desired product as a crystalline orange solid, m.p. 288°–289° C. (dec.).

EXAMPLE 2

Bis(dimethylhydrazone) of 9,10-anthracenedicarboxaldehyde dihydrochloride

A suspension of 4.68 g. of 9,10-anthracenedicarboxaldehyde in 200 ml. of ethanol containing 2.40 g. of unsymmetrical dimethylhydrazine and two drops of glacial acetic acid is stirred under reflux for two hours. The mixture is filtered while hot. The filtrate deposits the desired product as an orange solid, m.p. 177°–178° C.

EXAMPLE 3

N,N-Dimethylglycine(9,10-anthrylenedimethylidyne)-dihydrazine dihydrochloride

A suspension of 4.68 g. of 9,10-anthracenedicarboxaldehyde and 6.14 g. of N,N-dimethylglycyl hydrazine hydrochloride in 200 ml. of ethanol is stirred and heated under reflux for two hours. After the mixture is cool, the orange solid is collected and washed twice with ethanol. A turbid solution of this solid in 400 ml. of hot methanol is filtered, the filtrate is concentrated to 150 ml. and 150 ml. of diethyl ether is added. After standing overnight, the orange solid is collected and washed with acetone. A turbid solution of this solid in 200 ml. of methanol is chromatographed on silica gel, eluting with methanol. The eluate is allowed to stand 4 hours as it deposits a small amount of the solid, yellow free base [m.p. 276°–279° (dec.)] of the desired product. The filtrate from the yellow solid is evaporated giving an orange solid. A turbid solution of the orange solid in 150 ml. of hot methanol is filtered, concentrated to 50 ml., partly cooled, seeded and gradually diluted with 50 ml. of diethyl ether. The solid which separates is collected by filtration and washed with ethanol giving the desired dihydrochloride product as an orange solid, m.p. 277°–279° C. (dec.).

EXAMPLE 4

1,1'-[9,10-Anthrylenebis(methylidynenitrilo)]diguanidine dihydrochloride

A suspension of 3.51 g. of 9,10-anthracenedicarboxaldehyde and 4.08 g. of aminoguanidine bicarbonate in a mixture of 100 ml. of ethanol and 5.4 ml. of 8 N ethanolic hydrogen chloride is stirred and heated under reflux for two hours. The mixture is cooled and the solid is collected, washed four times with cold ethanol and dried, giving the desired product as an orange powder, m.p. 298°–301° C.

EXAMPLE 5

Bis(1,4,5,6-tetrahydro-2-pyrimidinylhydrazone) of 9,10-anthracenedicarboxaldehyde dihydrochloride 2-Hydrazino-1,4,5,6-tetrahydropyrimidine monohydroiodide (U.S. Pat. No. 3,931,152) is converted to the dihydrochloride by treatment with excess Dowex-2X8 ® (a strongly basic anion exchange resin in the hydrochloride form). The aqueous filtrate, upon being acidified with excess concentrated hydrochloric acid, gives the dihydrochloride salt. A mixture of 5.61 g. of the dihydrochloride and 3.51 g. of 9,10-anthracenedicarboxaldehyde in 100 ml. of ethanol is stirred and heated under reflux for two hours, then filtered. The chilled filtrate deposits a solid which is collected and washed three times with ethanol, giving the desired product as yellow crystals, m.p. 215°–230° C. (dec.).

EXAMPLE 6

Bis(4,5,6,7-tetrahydro-1H-1,3-diazepin-2-ylhydrazone) of 9,10-anthracenedicarboxaldehyde dihydroiodide A mixture of 7.68 g. of 2-hydrazino-4,5,6,7-tetrahydro-1H-1,3-diazepine hydroiodide (U.S. Pat. No. 3,931,152), 3.51 g. of 9,10-anthracenedicarboxaldehyde and 7.57 ml. of 4 N ethanolic hydrogen iodide, allowed to react as in Example 5, gives the desired product as an orange solid, m.p. 301°–302° C. (dec.).

EXAMPLE 7

1,1'-[9,10-Anthrylenebis(methylidynenitrilo)]bis-3-benzylguanidine dihydroiodide A mixture of 216 g. of thiosemicarbazide and 360 g. of iodomethane in 2.4 liters of absolute ethanol is heated under reflux for two hours and then allowed to cool overnight giving colorless crystals of S-methylisothiosemicarbazide hydroiodide. A mixture of 11.65 g. of this product and 10.9 ml. of benzylamine in 25 ml. of absolute ethanol is heated under reflux at 100° C. for one hour. The mixture is chilled and seeded and the product, 1-amino-3-benzylguanidine monohydroiodide, is collected as colorless crystals.

A suspension of 2.34 g. of 9,10-anthracenedicarboxaldehyde, 5.92 g. of 1-amino-3-benzylguanidine monohydroiodide and 5.8 ml. of 3.47 N ethanolic hydrogen iodide in 100 ml. of ethanol is stirred and heated under reflux for two hours, allowed to cool overnight, and the solid is collected and washed three times with diethyl ether giving the desired product as a yellow solid, m.p. 279°–282° C. (dec.).

EXAMPLE 8

1,1'-[9,10-Anthrylenebis(methylidynenitrilo)]bis(3-cyclohexylguanidine) dihydroiodide A solution of 2.8 g. of 1-amino-3-cyclohexylguanidine hydroiodide [W. G. Finnegan, R. A. Henry, E. Lisker, J. Org. Chem., 18, 779 (1952)] and 2.34 g. of anthracene-9,10-dicarboxaldehyde in 200 ml. of ethanol and 20 ml. of acetic acid is heated under reflux for 18 hours and filtered hot. The filtrate is evaporated to yield 5.0 g. of an orange solid. This is recrystallized from ethanol-ether to give the title compound; m.p. >300° C.

EXAMPLE 9

Bis(2-imidazolin-2-ylmethylhydrazone) of 9,10-anthracenedicarboxaldehyde dihydroiodide A solution of 48.8 g. of 2-methylthio-2-imidazoline hydroiodide and 10.0 g. of methylhydrazine in 200 ml. of ethanol is heated at reflux for several hours, clarified and then cooled at $-10°$ C. The precipitate is collected, washed with diethyl ether and dried, giving 2-(1-methylhydrazino)-imidazoline hydroiodide.

A suspension of 5.08 g. of 9,10-anthracenedicarboxaldehyde, 10.2 g. of 2-(1-methylhydrazino)imidazoline hydroiodide and 12.1 ml. of 3.47 N ethanolic hydrogen iodide in 135 ml. of ethanol is heated under reflux with stirring for two hours. The mixture is allowed to stand overnight and the solid is collected and washed three times with acetone giving the desired product, m.p. 298°–300° C. (dec.).

EXAMPLE 10

1,1'-[9,10-Anthrylenebis(methylidynenitrilo)]bis-3-methylguanidine dihydroiodide A suspension of 3.05 g. of 9,10-anthracenedicarboxaldehyde, 5.63 g. of 1-amino-3-methylguanidine hydroiodide [Kirsten et al., J.A.C.S. 58, 800 (1936)] and 7.50 ml. of 3.47 N ethanolic hydrogen iodide in 100 ml. of ethanol is heated under reflux with stirring for two hours and then chilled overnight. The mixture is evaporated to dryness, 40 ml. of methanol is added and the mixture is placed in an ice bath for 15 minutes. The solid is collected and washed three times with methanol giving the desired product, m.p. 247°–265° C. (dec.).

EXAMPLE 11

9,10-Anthracenedicarboxaldehyde bis(thiosemicarbazone)

A mixture of 2.34 g. of 9,10-anthracenedicarboxaldehyde and 3.65 g. of thiosemicarbazide in 250 ml. of absolute ethanol containing 2.0 ml. of glacial acetic acid is heated on a steam bath for 24 hours, allowed to cool and then let stand overnight. The solid is collected, washed with absolute ethanol, dried and recrystallized from aqueous dimethylformamide giving the desired product as orange crystals, m.p. 275°–277° C.

EXAMPLE 12

9,10-Anthracenedicarboxaldehyde disemicarbazone

A mixture of 2.34 g. of 9,10-anthracenedicarboxaldehyde, 4.46 g. of semicarbazide hydrochloride and 5.44 g. of sodium acetate in 250 ml. of absolute ethanol is heated at reflux for 24 hours, cooled and allowed to stand at room temperature. The solid is collected and recrystallized from a mixture of dimethylformamide and dimethylsulfoxide giving the desired product as yellow crystals, m.p. 300° C.

EXAMPLE 13

1,1'-(9,10-Anthrylenedimethylidyne)bis-3-thiocarbohydrazide

A mixture of 2.34 g. of 9,10-anthracenedicarboxaldehyde and 4.25 g. of thiocarbohydrazide in 250 ml. of absolute ethanol containing 2.0 ml. of glacial acetic acid is refluxed for 24 hours and then allowed to stand at room temperature. The solid is collected, washed with ethanol, dried and recrystallized from dimethylformamide giving the desired product, m.p. 252°–258° C. (dec.).

EXAMPLE 14

3,3'-[9,10-Anthrylenebis(methylidynenitrilo)]bis thiocarbazimidic acid dimethyl ester dihydroiodide A mixture of 2.34 g. of 9,10-anthracenedicarboxaldehyde and 4.66 g. of S-methylthiosemicarbazide hydroiodide in 250 ml. of absolute ethanol containing 2.0 ml. of glacial acetic acid is heated on a steam bath for 24 hours, cooled and allowed to stand for several hours. The solid is collected, washed with ethanol, dried and recrystallized from a mixture of dimethylformamide-ethanol-diethyl ether and petroleum ether giving the desired product as red-orange crystals, m.p. 225°–227° C. (dec.).

EXAMPLE 15

9,10-Anthracenedicarboxaldehyde bis(methylhydrazone)

A suspension of 4.68 g. of 9,19-anthracenedicarboxaldehyde and 1,84 g. of methyl hydrazine in 200 ml. of ethanol containing 2.0 drops of glacial acetic acid is stirred and heated under reflux for 1.5 hours. The mixture is cooled and the solid is collected and washed with ethanol giving the desired product as orange needles, m.p. 172°–174° C. (dec.).

EXAMPLE 16

N,N''-[9,10-Anthrylenedimethylidyne]bis[N',N'-dimethylethylenediamine]

A suspension of 4.68 g. of 9,10-anthracenedicarboxaldehyde and 5.29 g. of N,N-dimethylethylenediamine in 100 ml. of toluene is stirred and heated under reflux for 30 minutes collecting by-product water in a Dean-Stark trap. The solution is filtered and concentrated to 25 ml. Upon cooling, the reaction mixture gives a semi-solid mixture which is thoroughly macerated and dispersed in 75 ml. of petroleum ether (b.p. 35°–60° C.). The solid is collected and washed with petroleum ether giving the desired product as yellow leaflets, m.p. 108°–109° C.

EXAMPLE 17

1,1'-[9,10-Anthrylenebis(methylidynenitrilo)]bis-1-methylguanidine dihydrobromide A mixture of 2.3 g. of 9,10-anthracenedicarboxaldehyde, 3.4 g. of 1-amino-1-methylguanidine dihydrobromide, 200 ml. of ethanol and 1.3 ml. of 7.4 N HBr in ethanol was heated and stirred under reflux for 17 hours. The mixture was filtered hot to give 4.5 g. of product; m.p. 324°–325° C. (dec.).

EXAMPLE 18

1,1'-[9,10-Anthrylenebis)methylidynenitrilo)]bis[3,3-dimethyl-guanidine] dihydroiodide A mixture of 4.60 g. of 1-amino-3,3-dimethylguanidine hydroiodide [Finnegan et al., J. Org. Chem. 18 779 (1953)], 2.34 g. of 9,10-anthracenedicarboxaldehyde and 5.04 ml. of 4 N ethanolic hydrogen iodide in 100 ml. of ethanol is stirred and heated under reflux for two hours, then allowed to cool. The orange solid is collected and washed with ethanol, giving the desired product, m.p. 320°–322° C.

EXAMPLE 19

1,1'-[9,10-Anthrylenebis(methylidynenitrilo)]bis[1,3-dimethyl-guanidine] dihydroiodide A solution of 10.4 g. of N,N'-dimethylthiourea in 50 ml. of ethanol is treated with 14.5 g. of methyl iodide and heated under reflux for 70 minutes. The solution is filtered hot and cooled to give S-methyl-N,N'-dimethylisothiourea hydroiodide, m.p. 209°–212° C.

A solution of 17.5 g. of S-methyl-N,N'-dimethylisothiourea hydroiodide in 20 ml. of ethanol and 10 ml. of water is treated with 10 ml. of hydrazine hydrate and heated under reflux for 20 minutes. The mixture is cooled and the product is collected and washed with ethanol-water (2:1) and ether to give 13 g. of product. This is recrystallized from 150 ml. of boiling ethanol by adding water just to complete solution followed by cooling to give 1-amino-2,3-dimethyl-guanidine hydroiodide, m.p. 296°–298° C. Reaction of this salt according to the procedure of Example 18 followed by recrystallization from water gives the title compound as an orange solid, m.p. 281°–283° C.

EXAMPLE 20

1,1'-[9,10-Anthrylenebis(methylidynenitrilo)]bis[3-(2-hydroxyethyl)guanidine] dihydroiodide A solution of 11.6 g. of s-methylthiosemicarbazide hydroiodide and 3.2 ml. of ethanolamine in 50 ml. of ethanol is heated under reflux on a steam bath for 3 hours. The solution is cooled and treated with 15 ml. of 8 N ethanolic HCl cooled and diluted with diethyl ether to give a thick gum. The supernatant is decanted and the residue is dissolved in 60 ml. of hot ethanol, treated with about one ml. of water and cooled. A small amount of a solid is removed by filtration and the filtrate is treated with more ethanolic HCl to give a viscous gum. The supernatant is decanted, the residue (4,8 g.) is dissolved in 65 ml. of ethanol and treated with 1.9 g. of 9,10-anthracenedicarboxaldehyde and heated under reflux for 2.5 hours. The solution is filtered and cooled to give 1.7 g. of product. This product is recrystallized from 15 ml. of dimethylformamide (yield 1.0 g.) and then slurried in 6 ml. of methylcellosolve to give 450 mg. of an orange crystalline product; m.p. 234°–235° C.

EXAMPLE 21

1,1'-[9,10-Anthylenebis(methylidynenitrilo)]bis[3-(2-hydroxy-propyl)guanidine] dihydroiodide A solution of 32.0 g. of 1-(2-hydroxypropyl)imidazolidine-2-thione and 15 ml. of emthyl iodide in 250 ml. of isopropanol is stirred and heated under reflux for four hours, then cooled at −10° C. The precipitate, collected and washed with cold isopropanol and then with diethyl ether, is 1-(2-hydroxypropyl)-2-(methylthio)-2-imidazoline hydroiodide m.p. 114°–116° C. A solution of 30.2 g. of this salt and 5.2 ml. of hydrazine hydrate in 200 ml. of isopropanol is heated under reflux for four hours, filtered, then cooled at −10° C. The resulting precipitate, collected and washed with cold isopropanol and then with ether, is 2-hydrazino-1-(2-hydroxypropyl)-2-imidazoline hydroiodide, m.p. 140°–142° C. A mixture of 2.86 g. of this salt, 1.17 g. of 9,10-anthracenedicarboxaldehyde and 2.5 ml. of 4 N ethanolic hydrogen iodide, allowed to react as in Example 18 gives the title compound as a yellow solid, m.p. 249°–251° C. (dec.).

EXAMPLE 22

Bis(5-hydroxy-3,4,5,6-tetrahydropyrimidin-2-yl hydrazone) of 9,10-anthracenedicarboxaldehyde dihydrobromide A mixture of 26.4 g. of hexahydro-4-hydroxypyrimidine-2-thione and 30 ml. of ethyl bromide in 250 ml. of ethanol is stirred and heated under reflux for seven hours. Decolorizing charcoal is added, the solution filtered, cooled and diluted with 1 l. of ether. A thick oil separates. The mother liquor is discarded and the oil dried in vacuo. A mixture of 22.8 g. of the residue with 100 ml. of 95% ethanol and 5 ml. of hydrazine is stirred and heated under reflux for five hours as ethanethiol is evolved. The solution is evaporated to dryness in vacuo and the residue is dissolved in a boiling mixture of 100 ml. of isopropanol and 100 ml. of methanol. Decolorizing charcoal is added, the hot solution filtered, then cooled at −10° C. The resulting precipitate is collected and washed with cold 2-propanol and with ether. It is then recrystallized from isopropanol-methanol (1:1), using decolorizing charcoal, giving 2-hydrazino-5-hydroxy-3,4,5,6-tetrahydropyrimidine hydrobromide, m.p. 167°–169° C. A mixture of 1.19 g. of this salt and 1.32 g. of 9,10-anthracenedicarboxaldehyde in 40 ml. of ethanol and 0.95 ml. of 7.4 N ethanolic hydrogen bromide is allowed to react as in Example 18 to give the desired product as an orange-yellow solid.

EXAMPLE 23

1,1'-[9,10-Anthrylenebis(methylidynenitrilo)]bis-[3-(2-dimethylaminoethyl)guanidine] tetrahydroiodide A mixture of 216 g. of thiosemicarbazide and 360 g. of iodomethane in 2.4 liters of absolute ethanol is heated under reflux for 22 hours and then allowed to cool overnight, giving colorless crystals of S-methylthiosemicarbazide hydroiodide. A mixture of 11.65 g. of this product and 4.41 g. of N,N-dimethylethylenediamine in 25 ml. of absolute ethanol is heated under reflux at 100° C. for one hour. The mixture is cooled, diluted with ether and chilled. The product, 1-amino-3-(2-dimethylaminoethyl)guanidine hydroiodide, is collected as a colorless solid. A suspension of 2.34 g. of 9,10-anthracenedicarboxaldehyde in 200 ml. of absolute ethanol containing 5.46 g. of the guanidine salt and 5.8 ml. of 3.47 N ethanolic hydrogen iodide is stirred and heated under reflux for two hours. The mixture is allowed to cool, finally at 0° C., and the desired solid product is collected by filtration.

EXAMPLE 24

4-Morpholinecarboximidic acid, 2,2'-(9,10-anthrylenedimethylidyne)hydrazide dihydroiodide A solution of 4.65 g. of 4-morpholinethiocarboxamide [W. G. Finnegan, et al., J. Org. Chem. 18, 779 (1952)] and 4.54 g. of iodomethane in 50 ml. of ethanol is allowed to stand 48 hours at room temperature, then diluted with 250 ml. of ether to give a colorless crystalline precipitate of methyl 4-morpholinethiocarboximidate hydroiodide. A solution of 5.76 g. of this product and 1.1 g. of hydrazine hydrate in ethanol is heated under reflux for about 2 hours and then treated with 2.1 g. of 9,10-anthracenedicarboxaldehyde in 200 ml. of ethanol and 2 ml. of glacial acetic acid by heating under reflux for 3.5 hours. The solution is filtered and then evaporated to give an orange solid which is recrystallized from ethanol-ether to give the title compound, m.p. 280° C.

EXAMPLE 25

1,1'-[9,10-Anthrylenebis(methylidynenitrilo)]bis[3-(3-dimethylaminopropyl)-2-ethylguanidine] tetrahydrochloride Solid (3-dimethylaminopropyl)ethylcarbodiimide hydrochloride (3.82 g.) is added gradually with stirring to an ice-cooled solution of 1.00 g. of hydrazine hydrate in 75 ml. of water. The mixture is stirred for an hour without further cooling, chilled, strongly basified by the gradual addition of sodium hydroxide solution, then extracted with ether. The ether is dried over magnesium sulfate, filtered and evaporated. A solution of the residue in 100 ml. of ethanol is combined with 3 ml. of 8 N ethanolic hydrogen chloride and 2.34 g. of 9,10-anthracenedicarboxaldehyde, the resulting suspension is stirred and heated under reflux for two hours, then allowed to cool. The desired product separates after the addition of ether and is collected by filtration.

EXAMPLE 26

1,1'-[9,10-Anthrylenebis(methylidynenitrilo)]bisbiguanide tetrahydrochloride

A suspension of 3.36 g. of finely pulverized cyanoguanidine in 50 ml. of ethanol containing 2.00 g. of hydrazine hydrate is stirred and heated with an oil bath at 50° C. for five hours. After addition of 4.68 g. of anthracene 9,10-dicarboxaldehyde and 15.0 ml. of 8 N ethanolic hydrogen chloride the stirring and heating were continued for 15 hours. After the mixture had cooled the solid was collected by filtration and recrystallized from ethanol-water to give the desired product as an orange solid.

EXAMPLE 27

9,10-Anthracenedicarboxaldehyde bis(2-pyridylhydrazone)

A suspension of 4.68 g. of 9,10-anthracenedicarboxaldehyde in 200 ml. of ethanol containing 4.37 g. of 2-hydrazinopyridine and 2 drops of acetic acid is stirred and heated under reflux for two hours, then allowed to cool. Collection by filtration and washing with ethanol gives the desired product as an orange solid, which sinters from 267° C. to 272° C. (dec.).

EXAMPLE 28

9,10-Anthracenedicarboxaldehyde bis[(4-hydroxy-6-methyl-2-pyrimidinyl)hydrazone]

The procedure of the preceding example applied to 5.61 g. of 2-hydrazino-4-hydroxy-6-methylpyrimidine gives 10.0 g. of crude product as an orange solid which is purified by recrystallization from dimethylformamide.

EXAMPLE 29

9,10-Anthracenedicarboxaldehyde bis[(2-dimethylaminoethyl)hydrazone]

A suspension of 4.68 g. of anthracene-9,10-dicarboxaldehyde in 100 ml. of ethanol containing 4.13 g. of [2-(dimethylamino)ethyl]hydrazine [Elslager et al., J. Med. Chem. I, 493 (1964)] containing two drops of acetic acid is stirred and heated under reflux for two hours. The resulting solution is filtered, concentrated, allowed to cool to 45° C., diluted with petroleum ether, then allowed to cool further at 5° C. The desired product separates as an orange solid and is collected by filtration.

EXAMPLE 30

N,N"-[9,10-Anthrylenebis(methylidynenitrilo)]-diacetamidine dihydrochloride

A mixture of 4.68 g. of 9,10-anthracenedicarboxaldehyde and 4.38 g. of acetimidrazone hydrochloride [Neunhoeffer et al., Ann. 760, 102 (1972)] in 100 ml. of ethanol containing 5.0 ml. of 8 N ethanolic hydrogen chloride is heated under reflux with stirring for two hours, then allowed to cool. Collection by filtration and washing with cold ethanol affords the desired product as an orange solid.

EXAMPLE 31

Dibutyl 3,3'-(9,10-Anthrylenedimethylidyne)bis[thiocarbazimidate dihydroiodide]

A mixture of 2.34 g. of 9,10-anthracenedicarboxaldehyde and 5.0 of S-butylisothiosemicarbazide hydroiodide in 250 ml. absolute ethanol which contained 2 ml. of glacial acetic acid is heated at reflux for 24 hours, then cooled to room temperature. The crude product was isolated and recrystallized from dimethylformamide to yield 3.0 g. of orange-red crystals.

EXAMPLE 32

Dibenzyl 3,3'-(9,10-Anthrylenedimethylidyne)bis[thiocarboximidate dihydrochloride]

A mixture of 2.34 g. of 9,10-anthracenedicarboxaldehyde and 5.0 g. of S-benzylisothiosemicarbazide in 250 ml. of ethanol was treated as for the dibutyl ester to give the title compound.

EXAMPLE 33

9,10-Anthracenedicarboxaldehyde bis(4,4-dimethylthiosemicarbazone)

A mixture of 2.34 g. of 9,10-anthracenedicarboxaldehyde and 3.0 g. of 4,4-dimethylthiosemicarbazide in 250 ml. absolute ethanol containing 2.0 ml. glacial acetic acid is heated at reflux for 24 hours and then allowed to cool to room temperature. The crude solid is isolated by filtration, 1.83 g. of orange-red crystals.

EXAMPLE 34

4,Methyl-(9,10-anthrylenedimethylidyne)dihydrazide of 1-piperazinecarbothioic acid A mixture of 3.0 g. of 9,10-anthracenedicarboxaldehyde bis(thiosemicarbazone) and 25 ml. N-methylpiperazine was heated at 130° C. in an oil bath for 9 hours, then cooled to room temperature. The excess piperazine was removed under vacuum, the residual solid recrystallized twice from aqueous dimethylformamide to yield 1.0 g. of orange-red crystals.

EXAMPLE 35

1,1'-[9,10-Anthrylenebis(ethylidynenitriol)]diguanidine dihydrochloride

A suspension of 2.28 g. of 9,10-anthracenedicarbonitrile and 5.0 g. of methylmagnesium iodide in a solution of 50 ml. of ether and 50 ml. of toluene is heated to under reflux for 8 hours. The reaction product is collected, resuspended in ether and treated at −10° C. with a mixture of ice and ammonium chloride. The ether layer is dried over MgSO$_4$ and then saturated with hydrogen chloride to obtain the bis-ketimine dihydrochloride.

A solution of 3.33 g. of the bis-ketimine dihydrochloride, 2.72 g. of aminoguanidine bicarbonate and 1.6 g. of sodium acetate in 100 ml. of ethanol is heated under reflux for 10 hours. The mixture is cooled and filtered to obtain the desired compound.

EXAMPLE 36

1,1′[9,10-Anthrylenebis(phenylethylidynenitrilo)]-diguanidine dihydrochloride

A suspension of 2.28 g. of 9,10-anthracenedicarbonitrile and 6.0 g. of benzylmagnesium bromide was treated as in the preceding example to obtain the bis-ketimine dihydrochloride. A solution of 4.87 g. of this bis-ketimine dihydrochloride was treated as in the preceding example to obtain the title compound.

EXAMPLE 37

Bis(2-imidazolin-2-ylhydrazone) of 9,10-anthracenediacetaldehyde dihydrochloride A mixture of 2.56 g. of 9,10-anthracenediacetonitrile [J.A.C.S. 77, 2845 (1955)], 3.46 g. of 2-hydrazino-2-imidazoline dihydrochloride and 1.64 g. of sodium acetate in 50 ml. of 50% ethanol is reduced in the presence of 1.5 g. of Raney nickel until 2 molar equivalents of hydrogen are absorbed. The mixture is heated to boiling and filtered to remove the Raney nickel. The filtrate is evaporated to a small volume and cooled to give the desired product.

EXAMPLE 38

1,1′-[2-Methyl-9,10-anthrylenebis(methylidynenitrilo)]-diguanidine dihydrochloride A suspension of 2.48 g. of 2-methyl-9,10-anthracenedicarboxaldehyde (Example 51) and 2.72 g. of aminoguanidine bicarbonate in 100 ml. of ethanol and 3.6 ml. of 8 N ethanolic hydrogen chloride is stirred and heated under reflux for 2 hours. The mixture is cooled and the title compound is collected by filtration.

EXAMPLE 39

1,1′-[2,3,6,7-tetramethoxy-9,10-anthylenebis)methylidynenitrilo)]diguanidine dihydrochloride A suspension of 3.54 g. of 2,3,6,7-tetramethoxy-9,10-anthracenedicarboxaldehyde [C.A. 66, 2405n (1967)] and 2.72 g. of aminoguanidine bicarbonate in 100 ml. of ethanol and 3.6 ml. of 8 N ethanolic hydrogen chloride is stirred and heated under reflux for 18 hours. The mixture is cooled and the title compound [m.p. 314° C. (dec.)] is collected by filtration.

EXAMPLE 40

1,1′-[Ethyl-9,10-anthrylenebis(methylidynenitrilo)]-diguanidine dihydrochloride

A suspension of 2.72 g. of 2-ethyl-9,10-anthracenedicarboxaldehyde (Example 53) and 2.72 g. of aminoguanidine bicarbonate in 100 ml. of ethanol and 3.6 ml. of 8 N ethanolic hydrogen chloride is stirred and heated under reflux for 2 hours. The mixture is cooled and the title compound is collected by filtration.

EXAMPLE 41

[Bis(2-imidazolin-2-ylhydrazone)] of 2-chloro-9,10-anthracenedicarboxaldehyde dihydrochloride A reaction mixture comprising 1.34 g. of 2-chloro-9,10-anthracenedicarboxaldehyde and 1.73 g. of 2-hydrazinoimidazoline dihydrochloride in 80 ml. of ethanol is refluxed for two hours, and filtered while hot. After cooling, the solution deposited 0.7 g. of the desired product as orange crystals, m.p. ≧ 280° C.

EXAMPLE 42

1,1′-[2-Nitro-9,10-anthrylenebis(methylidynenitrilo)]-diguanidine dihydrochloride A suspension of 2.8 g. of 2-nitro-9,10-anthracenedicarboxaldehyde and 2.72 g. of aminoguanidine bicarbonate in 100 ml. of ethanol and 3.6 ml. of 8 N ethanolic hydrogen chloride is stirred and heated under reflux for 2 hours. The mixture is cooled and the title compound is collected.

EXAMPLE 43

1,1′-[2,6-Dihydroxy-9,10-anthrylenebis(methylidynenitrilo)]diguanidine dihydrochloride A suspension of 2.66 g. of 2,6-dihydroxy-9,10-anthracenedicarboxaldehyde (Example 57) and 2.72 g. of aminoguanidine bicarbonate in 100 ml. of ethanol and 3.6 ml. of 8 N ethanolic hydrogen chloride is stirred and heated under reflux for 2 hours. The mixture is cooled and the title compound is collected by filtration.

EXAMPLE 44

1,1′-[2,6-Dimethoxy-9,10-anthrylenebis(methylidynenitrilo)]diguanidine dihydrochloride A suspension of 2.94 g. of 2,6-dimethoxy-9,10-anthracenedicarboxaldehyde (Example 58) and 2.72 g. of aminoguanidine bicarbonate in 100 ml. of ethanol and 3.6 ml. of 8 N ethanolic hydrogen chloride is stirred and heated under reflux for 2 hours. The mixture is cooled and the title compound is collected.

EXAMPLE 45

Bis(2-imidazolin-2-ylhydrazone) of 2,6-diacetoxy-9,10-anthracenedicarboxaldehyde dihydrochloride A suspension of 3.5 g. of 2,6-diacetoxy-9,10-anthracenedicarboxaldehyde (Example 59) and 3.46 g. of 2-hydrazino-2-imidazoline dihydrochloride in 100 ml. of ethanol is stirred and heated under reflux for 2 hours. The mixture is cooled and the product is collected.

EXAMPLE 46

Bis(2-imidazolin-2-ylhydrazone) of 2-hydroxy-9,10-anthracenedicarboxaldehyde dihydrochloride A suspension of 2.5 g. of 2-hydroxy-9,10-anthracenedicarboxaldehyde (Example 60) and 3.46 g. of 2-hydrazino-2-imidazoline dihydrochloride in 100 ml. of ethanol is stirred and heated under reflux for 2 hours. The mixture is cooled and the product is collected by filtration.

EXAMPLE 47

Bis(2-imidazolin-2-ylhydrazone) of 1,2-dihydroxy-9,10-anthracenedicarboxaldehyde dihydrochloride A suspension of 2.66 g. of 1,2-dihydroxy-9,10-anthracenedicarboxaldehyde (Example 61) and 3.46 g. of 2-hydrazino-2-imidazoline dihydrochloride in 100 ml. of ethanol is stirred and heated under reflux for 2 hours. The mixture is cooled and the product is collected.

EXAMPLE 48

Bis(2-imidazolin-2-ylhydrazone) of 1,4-dihydroxy-9,10-anthracenedicarboxaldehyde dihydrochloride A suspension of 2.66 g. of 1,4-dihydroxy-9,10-anthracenedicarboxaldehyde (Example 62) and 3.46 g. of 2-hydrazino-2-imidazoline dihydrochloride in 100 ml. of ethanol is stirred and heated under reflux for 2 hours. The mixture is cooled and the product is collected.

EXAMPLE 49

Bis(2-imidazolin-2-ylhydrazone) of 2-amino-9,10-anthracenedicarboxaldehyde dihydrochloride A suspension of 2.5 g. of 2-amino-9,10-anthracenedicarboxaldehyde (Example 63) and 3.46 g. of 2-hydrazino-2-imidazoline dihydrochloride in 100 ml. of ethanol is stirred and heated under reflux for 2 hours. The mixture is cooled and the compound is collected by filtration.

EXAMPLE 50

2-Chloro-9,10-anthracenedicarboxaldehyde

A solution of 15.0 g. of 2-chloroanthracene in 60.8 g. of vinylene carbonate is heated under reflux for 20 hours. The excess vinylene carbonate is removed by vacuum distillation. The residue, a brown solid, is recrystallized from methylene chloride-methanol to give 2-chloro-9,10-dihydro-9,10-ethanoanthracene-11,12-diol cyclic carbonate, m.p. 200°–230° C.

A mixture of 12.0 g. of this cyclic carbonate and 9.2 g. of potassium hydroxide in 100 ml. of water and 12 ml. of ethanol is heated at 75° for 2 hours. The mixture is evaporated under reduced pressure to a volume of 50 ml. and then treated with 400 ml. of water. The crystalline product is collected and recrystallized from toluene to give 2-chloro-9,10-dihydro-9,10-ethanoanthracene-11,12-diol, m.p. 195°–210° C.

To a suspension of 2.73 g. of this diol in 70 ml. of acetic acid at 35° C. is added potassium 8.8 g. of lead tetraacetate during a 5-minute period. The reaction mixture is stirred at 35° C. for another two hours to give 1.5 g. of an orange crystalline compound. Evaporation of the mother liquor gives another 0.5 g. of compound. The two crops are combined and recrystallized from 50 ml. of toluene to give 2-chloro-9,10-anthracenedicarboxaldehyde, m.p. 193°–196° C.

EXAMPLE 51

2-Methyl-9,10-anthracenedicarboxaldehyde

Thirteen grams of 2-methylanthracene is converted to 2-methyl-9,10-anthracene-dicarboxaldehyde by the three step process described for the 2-chloro analog in Example 50; m.p. 162°–164° C.

EXAMPLE 52

1-Chloro-9,10-anthracenedicarboxaldehyde

Fifteen grams of 1-chloroanthracene is converted to 1-chloro-9,10-anthracenedicarboxaldehyde by the three step process described in Example 50.

EXAMPLE 53

2-Ethyl-9,10-anthracenedicarboxaldehyde

Fourteen grams of 2-ethylanthracene is converted to 2-ethyl-9,10-anthracenedicarboxaldehyde by the three step process described in Example 50; m.p. 99°–100° C.

EXAMPLE 54

9,10-Bis(chloromethyl)-2-methylanthracene

A mixture of 35 ml. of dioxane and 6 ml. of concentrated hydrochloric acid is saturated with hydrogen chloride gas. Then, 4.5 g. of 2-methylanthracene and 3.8 g. of 95% paraformaldehyde is added. The mixture is stirred slowly and heated under reflux while hydrogen chloride gas is introduced for 2 hours. The mixture is stirred and heated under reflux for 3 hours longer and then allowed to stand at room temperature for 16 hours. The yellow solid is collected by filtration, washed with dioxane, and dried to give the title compound.

EXAMPLE 55

2-Methyl-9,10-anthracenedicarboxaldehyde

To a stirred suspension of 2.6 g. of 9,10-bis-(chloromethyl)-2-methylathracene in 50 ml. of dimethyl sulfoxide (dried over calcium hydride) under nitrogen at room temperature is added slowly a solution prepared by adding 3.0 g. of 2-nitropropane to a solution of 0.5 g. of sodium in 30 ml. of ethanol. The reaction mixture gradually changes from yellow to dark orange and becomes homogenous. At this point (2.5 to 3.0 hours) the mixture is filtered into 200 ml. of ice-water. The orange precipitate is collected and redissolved in methylene chloride which is then extracted with water. The methylene chloride solution is dried over $MgSO_4$ and evaporated to dryness to give the title compound.

EXAMPLE 56

1-Methyl-9,10-anthracenedicarboxaldehyde

1-Methylanthracene (4.5 g.) is converted to 1-methyl-9,10-anthracene dicarboxaldehyde by the procedure described for the 2-methyl derivative.

EXAMPLE 57

2,6-Dihydroxy-9,10-anthracenedicarboxaldehyde

A suspension of 2.4 g. (0.01 mole) of 2,6-dihydroxy anthraquinone in 100 ml. of dry tetrahydrofuran containing 2.1 g. of triethylamine is treated with 2.2 g. of trimethylsilyl chloride and allowed to react until the anthraquinone dissolves. The triethylamine hydrochloride is filtered off and the remaining solution of silated anthraquinone is used as is in the following reaction.

In a dry system protected from moisture and under an atmosphere of argon, the solution of 0.01 mole of silated anthraquinone in tetrahydrofuran at room temperature is treated slowly with a solution of 0.02 mole of [α-lithio-α-(N,N-dimethylamino)methyl]diphenylphosphine oxide [Peterson, J. Am. Chem. Soc. 93, 4027

(1971)] in anhydrous ether-hexane. The reaction is allowed to proceed for two hours maintaining the temperature at room temperature with an ice bath.

The solution of the enamine is hydrolyzed at room temperature by the addition of 20 ml. of 90% formic acid solution. The reaction mixture is filtered, washed with water, dried and recrystallized from toluene giving 2,6-dihyroxy-9,10-anthracene dialdehyde.

Using well-known procedures, 2,6-dihydroxy-9,10-anthracenedicarboxaldehyde can be converted to the 2,6-dialkoxy- and 2,6-diacyloxy- derivatives.

EXAMPLE 58

2,6-Dimethoxy-9,10-anthracene-dicarboxaldehyde

A suspension of 2.66 g. (0.01 mole) of 2,6-dihydroxy-9,10-anthracenedicarboxaldehyde in 100 ml. of toluene is treated with 0.02 mole of petroleum ether-washed sodium hydride and is warmed gently with stirring until evolution of hydrogen ceased. The cooled reaction mixture is then treated with 0.02 mole of petroleum ether-washed sodium hydride and is warmed gently with stirring until evolution of hydrogen ceases. The cooled reaction mixture is then treated with 2.84 g. (0.02 mole) of methyl iodide and is stirred at 40° C. overnight, then is heated to reflux, filtered hot to remove the sodium iodide and allowed to cool giving crystals of 2,6-dimethoxy-9,10-anthracenedicarboxaldehyde.

EXAMPLE 59

2,6-Diacetoxy-9,10-anthracenedicarboxaldehyde

A solution of 2.66 g. (0.01 mole) of 2,6-dihydroxy-9,10-anthracenedicarboxaldehyde in 100 ml. of hot glacial acetic acid is treated with 2.5 g. (0.025 mole) of acetic anhydride. The mixture is stirred, heated on a steam for one hour, then allowed to cool yielding crystals of 2,6-diacetoxy-9,10-anthracenedicarboxaldehyde.

EXAMPLE 60

2-Hydroxy-9,10-anthracenedicarboxaldehyde

A suspension of 2.24 g. (0.01 mole) of 2-hydroxy anthraquinone in 100 ml. of dry tetrahydrofuran containing 1.05 g. (0.01 mole) of triethtylamine is treated with 1.1 g. (0.01 mole) of trimethylsilyl chloride and allowed to react until the anthraquinone dissolves. The triethylamine hydrochloride is filtered off and the remaining solution of silated anthraquinone is used as is in the following reaction.

In the same system as described for the 2,6-dihydroxy analog, a solution of 0.01 mole of the silated 2-hydroxy-anthraquinone in tetrahydrofuran is treated slowly with a solution of 0.01 mole of the same lithio anion. The reaction is allowed to proceed for two hours at room temperature. This solution of the enamine is hydrolyzed at room temperature by addition of 20 ml. of 90% formic acid solution. The reaction mixture is filtered, washed with water, dried and recrystallized from toluene giving 2-hydroxy-9,10-anthracene dicarboxaldehyde.

EXAMPLE 61

1,2 Dihydroxy-9,10-anthracenedicarboxaldehyde

Starting with 2.4 g. (0.01 mole) of 1,2-dihydroxyanthraquinone and using the same three-step procedure described above for the 2,6-dihydroxy analog, there is obtained 1,2-dihydroxy-9,10-anthracene dicarboxaldehyde as colorless crystals from toluene.

EXAMPLE 62

1,4-Dihydroxy-9,10-anthracenecarboxaldehyde

Starting with 2.4 g. (0.01 mole) of 1,4-dihydroxy anthraquinone and using the same three-step procedure as for the 2,6-dihydroxy analog, there is obtained 1,4-dihydroxy-9,10-anthracene dicarboxaldehyde as crystals from toluene.

EXAMPLE 63

2-Amino-9,10-anthracenedicarboxaldehyde

Starting with 2.3 g. (0.01 mole) of 2-aminoanthraquinone and following the same procedure as described for the 2-hydroxy analog, there is obtained 2-amino-9,10-anthracenedicarboxaldehyde.

EXAMPLE 64

9,10-Anthracenedicarboxaldehyde

A solution of 2.38 g. (0.01 mole) of cis-9,10-dihydro-9,10-ethanoanthracene-11,12-diol [Newman et al., J. Am. Chem. Soc., 77, 3789 (1955)] in 50 ml. of glacial acetic acid was stirred magnetically at 30°–35° C. and treated portionwise with 8.9 g. (0.02 mole) of lead tetraacetate or until a blue color persisted with starch-iodide test paper. The reaction mixture was stirred for two hours and the so-formed orange crystals were removed by filtration and recrystallized from methylene chloride giving 1.5 g. (65%) of orange needles, m.p. 245°–247° C.

EXAMPLE 65

1,1'-[9,10-Anthrylenebis(methylidynenitrilo)]bis[3-furfurylguanidine] dihydrochloride A mixture of 1.0 g. of 9,10-anthracenedicarboxaldehyde, 2.0 g. of 1-amino-3-furylguanidine dihydrochloride and 100 ml. of ethanol is heated under reflux for 1.5 hours. The solution is evaporated to give a glassy residue which is ground and triturated with diethyl ether to give an orange powder weighing 2.0 g.; m.p. 135°–140° C. (dec.).

EXAMPLE 66

1,1'-[9,10-Anthrylenebis(methylidynenitrilo)]bis[3-(2-thenyl)guanidine] dihydrochloride A mixture of 2.0 g. of 0.96 g. of 9,10-anthracenedicarboxaldehyde, 2.0 g. of 1-amino-3-thenylguanidine dihydrochloride, 75 ml. of ethanol and 0.3 ml. of concentrated HCl is heated under reflux for 2.5 hours. The solution is cooled and filtered to remove a small amount of solid and then evaporated to dryness. The residue is evaporated three times with methanol and then dissolved in a small amount of methanol and treated with a large amount of diethyl ether to give a gummy solid. The supernatant is decanted and the residue is slurried with more ether to obtain a yellow solid; yield 2.2 g.; m.p. 190°–200° C. (dec.).

EXAMPLE 67

1,1'-[9,10-Anthrylenebis(methylidynenitrilo)]bis[2,3-diisopropylguanidine] dihydroiodide A mixture of 4.0 g. of 1-amino-2,3-diisopropyl guanidine hydroiodide, 1.6 g. of 9,10-anthracenedicarboxaldehyde, 100 ml. of ethanol and 2 ml. of 4 N ethanolic hydrogen iodide is heated under reflux for 4 hours. The mixture is filtered hot to remove a little solid and the filtrate is concentrated to the appearance of an orange crystalline product. The suspension is cooled and filtered to give 4.4 g. of product; m.p. 278°–280° C.

EXAMPLE 68

1,1'-[9,10-Anthrylenebis(methyldynenitrilo)]bis[3-(1-indanyl)guanidine] dihydroiodide A solution of 1.14 g. of 9,10-anthracenedicarboxaldehyde and 3.1 g. of 1-amino-3(1-indanyl)guanidine in 50 ml. of ethanol containing 3 ml. of 4 N ethanolic HI is heated under reflux for 3 hours and then cooled overnight to give 2.3 g. of orange crystalline product; m.p. 262°–263° C.

EXAMPLE 69

1,1'-[9,10-Anthrylenebis(methylidynenitrilo]bis[3-(4-pyridylmethyl)guanidine] tetrahydroiodide A mixture of 2.3 g. of 9,10-anthracenedicarboxaldehyde, 6.4 g. of 1-amino-3-(4-pyridylmethyl)guanidine, 9.0 ml. of 4 N HI and 100 ml. of ethanol is heated under reflux for 3 hours and cooled to give 6.3 g. of solid. 3.9 g. of this product is slurried in 160 ml. of ethanol which is brought to boiling, treated dropwise with water until solution occurrs. This is treated with a little Darco ®, filtered and cooled to give 2.2 g. of product; m.p. 235°–240° C. (dec.).

EXAMPLE 70

2-Methyl-9,10-anthracenedicarboxaldehyde

A mixture of isomers of 2-methyl-11,12-dihydroxy-9,10-ethano-anthracene weighing 2.1 g. is dissolved in 45 ml. of glacial acetic acid and is treated at room temperature with 7.45 g. of lead tetraacetate until a starch-iodide test is positive. After 2–3 hours at room temperature followed by cooling there is deposited orange crystals, which are collected by filtration and recrystallized from methylene chloride-methanol giving 1.1 g. of orange crystals melting at 162°–164° C.

EXAMPLE 71

Bis(2-imidazolin-2-ylhydrazone] of 2-methyl-9,10-Anthracenedicarboxaldehyde dihydrochloride monohydrate A solution of 2.2 g. of 2-methyl-9,10-anthracenedicarboxaldehyde in 150 ml. of boiling n-propanol is treated with 3.1 g. of 2-imidazolin-2-ylhydrazine. The solution is boiled and concentrated over the course of 2 hours to 100 ml., whereupon it is filtered to clarify and cooled. After long standing there is deposited 2.2 g. of orange crystals melting at 300°–302° C.

The free base of the above product may be obtained as red-orange crystals by basifying the mother liquor with aqueous sodium bicarbonate solution, m.p. 295°–298° C.

EXAMPLE 72

1,4-Dimethoxy-9,10-anthracenedicarboxaldehyde

A mixture of isomers of 1,4-dimethoxy-11,12-dihydroxy-9,10-ethano-anthracene weighing 10 g. is dissolved in 150 ml. of glacial acetic acid at 50° C. and treated portionwise with 30 g. of lead tetraacetate. After 2 hours at 50° C., the solution is filtered to remove insoluble materials and cooled yielding orange crystals, which are filtered, washed with glacial acetic acid and dried, m.p. 208°–212° C.

EXAMPLE 73

Bis[1,4-Dimethoxy-bis(2-imidazolin-2-ylhydrazone)] of 9,10-Anthracenedicarboxaldehyde dihydrochloride A solution of 1.7 g. of 1,4-dimethoxy-9,10-anthracene dicarboxaldehyde in 100 ml. of n-propanol is treated with 2.06 g. of 2-imidazolin-2-ylhydrazine and boiled for 2 hours while concentrating to 50 ml. The hot solution is filtered to give a yellow solid which is washed with n-propanol and dried, m.p. 300°–305° C.

EXAMPLE 74

Bis(2-imidazolin-2-ylhydrazone) of 2,6-difluoro-9,10-anthracenedicarboxaldehyde

A suspension of 2.74 g. of 2,6-difluoro-9,10-anthracenedicarboxaldehyde (Example 75) and 3.46 g. of 2-hydrazino-2-imidazoline dihydrochloride in 100 ml. of ethanol is stirred and heated under reflux for 3 hours. The mixture is cooled and the product is collected by filtration; m.p.>320° C.

EXAMPLE 75

2,6-Difluoro-9,10-anthracenedicarboxaldehyde 15 g. of 2,6-difluoroanthracene is converted to 2,6-difluoro-9,10-anthracenedicarboxaldehyde by the three-step process described in Example 50; m.p. 240°–242° C.

EXAMPLE 76

Bis(2-imidazolin-2-ylhydrazone) of 2,3-dimethyl-9,10-anthracenedicarboxaldehyde

A suspension of 2.7 g. of 2,3-dimethyl-9,10-anthracenedicarboxaldehyde (Example 77) and 3.46 g. of 2-hydraaino-2-imidazoline dihydrochloride in 100 ml. of ethanol is stirred and heated under reflux for 3 hours. The mixture is cooled and the product is collected; m.p. 300°–305° C.

EXAMPLE 77

2,3-Dimethyl-9,10-anthracenedicarboxaldehyde 14 g. of 2,3-dimethylanthracene is converted to 2,3-dimethyl-9,10-anthracenedicarboxaldehyde by the three-step process described in Example 50; m.p. 203°–204° C.

EXAMPLE 78

Bis(2-imidazolin-2-ylhydrazone) of 2,6-dichloro-9,10-anthracenedicarboxaldehyde dihydrochloride A suspension of 3.03 g. of 2,6-dichloro-9,10-anthracenedicarboxaldehyde and 3.46 g. of 2-hydrazino-2-imidazoline dihydrochloride in 100 ml. of ethanol is heated under reflux for 3 hours and cooled to give the title compound.

EXAMPLE 79

2,6-Dichloro-9,10-anthracenedicarboxaldehyde 18 g. of 2,6-dichloroanthracene is converted to 2,6-dichloro-9,10-anthracenedicarboxaldehyde by the three-step process described in Example 50.

EXAMPLE 80

Bis(2-imidazolin-2-ylhydrazone) of 1,4-dimethyl-9,10-anthracenedicarboxaldehyde dihydrochloride A suspension of 2.6 g. of 1,4-dimethyl-9,10-anthracenedicarboxaldehyde and 3.46 g. of 2-hydrazino-2-imidazoline dihydrochloride in 100 ml. of ethanol is heated under reflux for 2 hours and cooled to give the title compound; m.p. 185°–190° C.

EXAMPLE 81

1,4-Dimethyl-9,10-anthracenedicarboxaldehyde 16 g. of 1,4-dimethylanthracene is converted to 1,4-dimethyl-9,10-anthracenedicarboxaldehyde by the three-step procedure described in Example 50; m.p. 158°–162° C.

EXAMPLE 82

Bis(2-imidazolin-2-ylhydrazone) of 1,5-difluoro-9,10-anthracenedicarboxaldehyde, dihydrochloride A mixture of 1.0 g. of 1,5-difluoro-9,10-anthracenedicarboxaldehyde, 1.3 g. of 2-hydrazinoimidazoline dihydrochloride and 150 ml. of isopropanol is heated to boiling for 4 hours and cooled to obtain 1.75 g. of product, m.p. 309° C. (dec.).

EXAMPLE 83

Bis(2-imidazolin-2-ylhydrazone) of fluoro-9,10-anthracenedicarboxaldehyde, dihydrochloride A mixture of 0.6 g. of 2-fluoro-9,10-anthracenedicarboxaldehyde, 0.84 g. of 2-hydrazinoimidazoline dihydrochloride and 70 ml. of n-propanol is heated under reflux for 2.5 hours. The solution is evaporated to ½ its volume and cooled to obtain 1.0 g. of the product, m.p. 300° C. (dec.).

EXAMPLE 84

Bis(2-imidazolin-2-ylhydrazone) of 1-fluoro-9,10-anthracenedicarboxaldehyde, dihydrochloride A mixture of 0.6 g. of 1-fluoro-9,10-anthracenedicarboxaldehyde, 0.84 g. of 2-hydrazinoimidazoline dihydrochloride and 70 ml. of n-propanol is heated under reflux for 2.5 hours, evaporated to ½ volume, cooled and treated with hexane to obtain 1.0 g. of the product, m.p. 215°–220° C.

EXAMPLE 85

Bis(2-imidazolin-2-ylhydrazone) of 1-chloro-9,10-anthracenedicarboxaldehyde, dihydrochloride A mixture of 2.2 g. of 1-chloro-9,10-anthracenedicarboxaldehyde, 2.84 g. of 2-hydrazinoimidazoline and 250 ml. of 1-propanol is heated under reflux for 1.5 hours, evaporated to a volume of 125 ml. and cooled to give 2.7 g. of the product in the form of orange crystals, m.p. 230° C. (dec.).

EXAMPLE 86

Bis(2-imidazolin-2-ylhydrazone) of 1-chloro-2-methyl-9,10-anthracenedicarboxaldehyde, dihydrochloride A mixture of 0.43 g. of 1-chloro-2-methyl-9,10-anthracenedicarboxaldehyde, 0.53 g. of 2-hydrazinoimidazoline, dihydrochloride and 40 ml. of n-propanol is heated to boiling for 1.5 hours, evaporated to a 20 ml. volume, cooled and treated with ether to obtain 0.75 g. of the product, m.p. 215°–220° C.

EXAMPLE 87

1,1'-[2-Chloro-9,10-anthrylenebis(methylidynenitrilo)]-bis[3,3-dimethylguanidine] dihydroiodide A mixture of 2.7 g. of 2-chloro-9,10-anthracenedicarboxaldehyde, 4.6 g. of 1-amino-2,2-dimethylquanidine hydroiodide, 250 ml. of n-propanol and 5 drops of 57% hydriodic acid is heated under reflux for 1.5 hours, evaporated to ½ its volume and cooled to give 5.7 g. of the product, m.p. 301°–303° C.

EXAMPLE 88

Bis(1,4,5,6-tetrahydro-2-pyrimidinylhydrazone) of 2-chloro-9,10-anthracenedicarboxaldehyde, dihydrochloride A mixture of 2.7 g. of 2-chloro-9,10-anthracenedicarboxaldehyde, 3.74 g. of 2-hydrazino-1,4,5,6-tetrahydropyrimidine dihydrochloride and 270 ml. of n-propanol is heated under reflux for 1.5 hours, evaporated to ½ its volume, cooled and filtered to give 1.9 g. of the product.

EXAMPLE 89

1,1'-[9,10-Anthrylenebis(methylidynenitrilo)]bis[3-(4-pyridylmethyl)guanidine] tetrahydrochloride A mixture of 3.5 g. of 9,10-anthracenedicarboxaldehyde, 7.4 g. of 1-amino-2-(pyrid-4-ylmethyl)guanidine dihydrochloride, 150 ml. of ethanol and 10 ml. of water is heated under reflux for 4 hours. The mixture is cooled to room temperature and the product is collected to give 9.5 g. of the product, m.p. 299°–302° C.

EXAMPLE 90

1,1'-[9,10-Anthrylenebis(methylidynenitrilo)]bis[3-(3-pyridylmethyl)guanidine] tetrahydrochloride A mixture of 0.98 g. of 9,10-anthracenedicarboxaldehyde, 2.3 g. of 1-amino-3-(pyrid-3-ylmethyl)quanidine dihydrochloride, 40 ml. of ethanol and 2 ml. of water is heated under reflux for 2.5 hours, cooled to room temperature and filtered to give 2.6 g. of the product, m.p. 298°–302° C.

EXAMPLE 91

1,1'-[9,10-Anthrylenebis(methylidynenitrilo)]bis[3-(2-pyridylmethyl)guanidine] tetrahydrochloride A mixture of 3.5 g. of 9,10-anthracenedicarboxaldehyde, 7.4 g. of 1-amino-2-(pyrid-2-ylmethyl)guanidine dihydrochloride and 150 ml. of ethanol is heated under reflux for 4 hours, cooled and filtered to give 9.9 g. of the product, m.p. 285°–290° C.

EXAMPLE 92

Bis(2-imidazolin-2-ylhydrazone) of 2-ethyl-9,10-anthracenedicarboxaldehyde, dihydrochloride A mixture of 3.0 g. of 2-ethyl-9,10-anthracenedicarboxaldhyde, 4.0 g. of 2-hydrazinoimidazoline dihydrochloride and 200 ml. of n-propanol is heated to boiling for 2 hours and concentrated to a volume of 50 ml. This is cooled to give 3.1 g. of the product (orange crystals), m.p. 287°–290° C.

EXAMPLE 93

1,1'-[2-Chloro-9,10-anthrylenebis(methylidynenitrilo)]-diguanidine, dihydrochloride A mixture of 2.7 g. of 2-chloro-9,10-anthracenedicarboxaldehyde, 2.7 g. of aminoguanidine bicarbonate, 3.0 ml. of 6.55 N hydrogen chloride in n-propanol and 250 ml. of n-propanol is heated under reflux for 1.5 hours. The solution is evaporated to ½ its volume and cooled to give 1.0 g. of the product in the form of orange crystals, m.p. 322°–324° C.

EXAMPLE 94

9,10-Anthracenedicarboxaldehyde, bis(4,5,6,7-tetrahydro-3H-azepin-2-ylhydrazone) dihydrochloride A mixture of 4.3 g. of 9,10-anthracenedicarboxaldehyde and 5.1 g. of 2-hydroxy-4,5,6,7-tetrahydro-3H-azepine, 100 ml. of water and 10 ml. of 8 N ethanolic hydrogen chloride is heated under reflux for 2.75 hours, filtered, cooled to room temperature, treated with ether and cooled further to give 7.4 g. of crystalline product. This solid is recrystallized from 460 ml. of isopropanol-ethanol (3:1) to give 4.6 g. of product, m.p. 220°–225° C.

EXAMPLE 95

1,1'-[9,10-Anthrylenebis(methylidynenitrilo)]bis[3-(2-dimethylaminoethyl)guanidine] tetrahydrochloride A mixture of 3.5 g. of 9,10-anthracenedicarboxaldehyde, 8.3 g. of 1-amino-3-(dimethylaminoethyl)guanidine trihydrochloride, 150 ml. of ethanol and 8 ml. of water is heated under reflux for 2.5 hours, treated with charcoal and filtered. This solution is evaporated to dryness and reevaporated with ethanol. The residue is slurried with hot isopropanol, cooled and filtered to give 9.0 g. of orange solid.

EXAMPLE 96

9,10-Anthracenedicarboxaldehyde, bis[4-(3-dimethylaminopropyl)-3-thiosemicarbazone] dihydrochloride A mixture of 2.9 g. of 9,10-anthracenedicarboxaldehyde, 5.0 g. of 4-(3-dimethylaminopropyl)-3-thiosemicarbazide, 100 ml. of ethanol and 12 ml. of 8 N ethanolic hydrogen chloride is heated under reflux for 3.5 hours, filtered hot and cooled to give 5.7 g. of orange solid. This is recrystallized from 85 ml. of dimethylformamide to give 4.5 g. of product. After drying at 75° C. in a pistol it has a m.p. of 221°–223° C.

EXAMPLE 97

9,10-Anthracenedicarboxaldehyde, bis[4-(3-dimethylaminoethyl)-3-thiosemicarbazone] dihydrobromide A mixture of 3.5 g. of 9,10-anthracenedicarboxaldehyde, 5.4 g. of 4-(dimethylaminoethyl)thiosemicarbazide, 250 ml. of ethanol and 2 ml. of 48% hydrogen bromide is heated under reflux for 4 hours and filtered hot to give 6.4 g. of solid. This is resuspended in 175 ml. of boiling ethanol and treated with 20 ml. of 48% hydrogen bromide to obtain complete solution. This is cooled, treated with 100 ml. of ether and cooled further to give 3.1 g. of the product in the form of orange-red crystals, m.p. 289°–290° C.

EXAMPLE 98

9,10-Anthracenedicarboxaldehyde, bis(4,4-dimethyl-2-imidazolin-2-ylhydrazone) dihydrochloride A mixture of 2.34 g. of 9,10-anthracenedicarboxaldehyde, 4.4 g. of 4,4-dimethylimidazolin-2-ylhydrazine hydrobromide and 50 ml. of n-propanol is boiled for 2 hours. The yellow-orange solid is collected, washed with n-propanol and dried. This hydrobromide salt is dissolved in water and basified with sodium bicarbonate to give a solid which is collected, redissolved in 60 ml. of hot n-propanol and treated with 0.6 ml. of 7 N hydrochloric acid in isopropanol and cooled to give 1.2 g. of the title compound, m.p. 310°–315° C.

EXAMPLE 99

9,10-Anthracenedicarboxaldehyde, bis[(1,4,5,6-tetrahydro-5,5-dimethyl-2-pyrimidinyl)hydrazone, dihydrochloride A mixture of 0.94 g. of 9,10-anthracenedicarboxaldehyde, 1.7 g. of 5,5-dimethyl-1,4,5,6-tetrahydropyrimidin-2-yl-hydrazine and 50 ml. of n-propanol is heated to boiling for 0.5 hours, then cooled to give 1.7 g. of a yellow crystalline product, m.p. 340° C. (dec.).

We claim:

1. A compound selected from the group consisting of those of the formula:

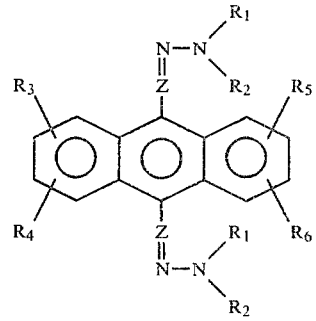

wherein Z is a trivalent moiety selected from the group consisting of those of the formulae:

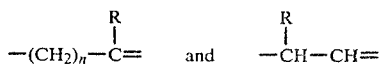

wherein n is 0, 1, 2 or 3 and R is hydrogen, alkyl having up to 4 carbon atoms, cycloalkyl having from 3 to 6 carbon atoms, phenyl or benzyl; $R_1$ is selected from the group consisting of hydrogen and alkyl having up to 4 carbon atoms; $R_2$ is selected from the group consisting of hydrogen, alkyl having up to 4 carbon atoms, phenyl and monovalent moieties of the formulae:

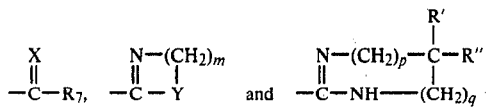

wherein m is 2, 3, 4 or 5, p is 1, 2 or 3, q is 0, 1 or 2, R' is hydrogen or alkyl having up to 4 carbon atoms, R'' is hydrogen or alkyl having up to 4 carbon atoms, $R_7$ is alkyl having up to 4 carbon atoms, amino, anilino, hydrazino, monohydroxyalkylamino having from 2 to 4 carbon atoms and wherein the carbon atom alpha to the nitrogen atom may not bear an hydroxy group, alkylamino having up to 4 carbon atoms, dialkylamino wherein each alkyl group has up to 4 carbon atoms, cycloalkylamino having from 3 to 6 carbon atoms, benzylamino, α-phenethylamino, β-phenethylamino, 2-furfurylamino, 3-furfurylamino, α-thenylamino, β-thenylamino, α-pyridylmethylamino, β-pyridylmethylamino, γ-pyridylmethylamino, indanylamino, pyrrolidino, piperidino, morpholino, thiomorpholino, N-methylpiperazino, alkoxy having up to 4 carbon atoms, alkylthio having up to 4 carbon atoms or a moiety of the formula:

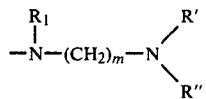

wherein m, $R_1$, R' and R'' are as hereinbefore defined and the moiety —NR'R'' may be pyrrolidino, piperidino, morpholino or N-methylpiperazino, X is oxo (O=), thioxo (S=) or imino (R'—N= wherein R' is as hereinbefore defined) and Y is oxy (—O—), thio (—S—), methylene (—CH$_2$—) or a divalent group of the formula:

wherein $R_8$ is alkyl having up to 4 carbon atoms or monohydroxyalkyl having from 2 to 4 carbon atoms and wherein the carbon atom alpha to the nitrogen atom may not bear an hydroxy group; and $R_3$, $R_4$, $R_5$ and $R_6$ are each individually selected from the group consisting of hydrogen, halogen (F, Cl, Br, I), hydroxy, nitro, amino, sulfonamido, alkyl having up to 3 carbon atoms and alkoxy having up to 3 carbon atoms; and the pharmacologically acceptable acid-addition and quaternary ammonium salts thereof.

2. The compound according to claim 1 wherein Z is methylidyne, $R_1$, $R_3$, $R_4$, $R_5$ and $R_6$ are hydrogen and $R_2$ is

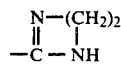

bis(2-imidazolin-2-yl)hydrazone of 9,10-anthracenedicarboxaldehyde dihydrochloride.

3. The compound according to claim 1 wherein Z is methylidyne, $R_1$, $R_3$, $R_4$, $R_5$ and $R_6$ are hydrogen and $R_2$ is

wherein X is imino and $R_7$ is methylamino; 1,1-[9,10-anthrylenebis(methylidynenitrilo)]bis-3-methylguanidine dihydroiodide.

4. The compound according to claim 1 wherein Z is methylidyne, $R_1$, $R_3$, $R_4$, $R_5$ and $R_6$ are hydrogen and $R_2$ is

wherein X is methylimino and $R_7$ is methylamino; 1,1'-[9,10-anthrylene-bis(methylidynenitrilo)]bis-(2,3-dimethylguanidine)dihydroiodide.

5. The compound according to claim 1 wherein Z is methylidyne, $R_1$, $R_3$, $R_4$, $R_5$ and $R_6$ are hydrogen and $R_2$ is

wherein X is imino and $R_7$ is dimethylamino; 1,1'-[9,10-anthrylenebis(methylidynenitrilo)]bis-(3,3-dimethylguanidine)dihydroiodide.

6. The compound according to claim 1 wherein Z is methylidyne, $R_1$, $R_3$, $R_4$, $R_5$ and $R_6$ are hydrogen and $R_2$ is

wherein X is imino and $R_7$ is hydroxyethylamino; 1,1'-[9,10-anthrylenebis(methylidynenitrilo)]bis-[3-(2-hydroxyethyl)guanidine]dihydroiodide.

7. The compound according to claim 1 wherein Z is methylidyne, $R_1$, $R_3$, $R_4$, $R_5$ and $R_6$ are hydrogen and $R_2$ is

wherein X is imino and $R_7$ is amino; 1,1'-[9,10-anthrylenebis(methylidynenitrilo)]diguanidine dihydrochloride.

8. The compound according to claim 1 wherein Z is methylidyne, $R_1$, $R_3$, $R_4$, $R_5$ and $R_6$ are hydrogen and $R_2$ is

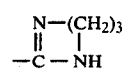

bis(1,4,5,6-tetrahydro-2-pyrimidin-2-ylhydrazone) of 9,10-anthracenedicarboxaldehyde dihydrochloride.

9. The compound according to claim 1 wherein Z is methylidyne, $R_1$ is methyl, $R_3$, $R_4$, $R_5$ and $R_6$ are hydrogen and $R_2$

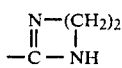

bis(2-imidazolin-2-ylmethylhydrazone) of 9,10-anthracenedicarboxaldehyde dihydroiodide.

10. The compound according to claim 1 wherein Z is methylidyne, $R_1$, $R_3$, $R_4$, $R_5$ and $R_6$ are hydrogen and $R_2$ is

wherein X is imino and $R_7$ is benzylamino; 1,1'-[9,10-anthrylenebis)methylidynenitrilo)]bis(3-benzylguanidine)dihydroiodide.

11. The compound according to claim 1 wherein Z=methylidyne, $R_1$, $R_3$, $R_4$, $R_5$ and $R_6$ are hydrogen and $R_2$ is

wherein X is imino and $R_7$ is 2-furfurylamino:1,1'[9,10-anthrylenebis(methylidynenitrilo)]bis[3-(2-furfuryl)-guanidine]dihydrochloride.

12. The compound according to claim 1 wherein Z is methylidyne, $R_1$, $R_3$, $R_4$, $R_5$ and $R_6$ are hydrogen and $R_2$ is

wherein X is imino and $R_7$ is cyclohexylamino; 1,1'-[9,10-anthrylenebis(methylidynenitrilo)]bis(3-cyclohexylguanidine)dihydroiodide.

13. The compound according to claim 1 wherein Z=methylidyne, $R_1$, $R_3$, $R_4$, $R_5$ and $R_6$ are hydrogen and $R_2$ is

wherein X is imino and $R_7$ is 2-thenylamino:1,1'-[9,10-anthrylenebis(methylidynenitrilo)]bis[3-(2-thenyl)-guanidine]dihydrochloride.

14. The compound according to claim 1 wherein Z=methylidyne, $R_1$, $R_3$, $R_4$, $R_5$ and $R_6$ are hydrogen and $R_2$ is

wherein X is imino and $R_7$ is 4-pyridylmethylamino:1,1'-[9,10-Anthrylenebis(methylidynenitrilo)]bis[3-(4-pyridylmethyl)guanidine]tetrahydroiodide.

15. The compound according to claim 1 wherein Z is methylidyne, $R_1$, $R_3$, $R_4$ and $R_6$ are hydrogen, $R_5$ is 2-chloro and $R_2$ is

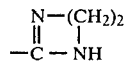

bis(2-imidazolin-2-ylhydrazone) of 2-chloro-9,10-anthracenedicarboxaldehyde dihydrochloride.

16. The compound according to claim 1 wherein Z is methylidyne, $R_1$, $R_3$, $R_4$ and $R_6$ are hydrogen, $R_5$ is 2-methyl and $R_2$ is

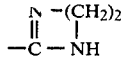

bis(2-imidazolin-2-ylhydrazone) of 2-methyl-9,10-anthracenedicarboxaldehyde dihydrochloride.

17. The compound according to claim 1 wherein Z=methylidyne, $R_5$ is 1-hydroxy, $R_6$ is 4-hydroxy, $R_1$, $R_3$ and $R_4$ are hydrogen and $R_2$ is

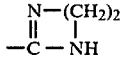

bis(2-imidazolin-2-ylhydrazone) of 1,4-dihydroxy-9,10-anthracenedicarboxaldehyde dihydrochloride.

18. The compound according to claim 1 wherein Z=methylidyne, $R_1$, $R_4$ and $R_6$ are hydrogen, $R_3$ and $R_5$ are fluorine, and $R_2$ is

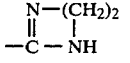

bis(2-imidazolin-2-ylhydrazone) of 2,6-difluoro-9,10-anthracenedicarboxaldehyde.

19. The compound according to claim 2 as the diacetate salt.

20. An acid-addition salt according to claim 1 wherein the acid is acetic acid.

21. An acid-addition salt according to claim 1 wherein the acid is hydrochloric acid.

22. An acid-addition salt according to claim 1 wherein the acid is maleic acid.

23. An acid-addition salt according to claim 1 wherein the acid is gluconic acid.

* * * * *